United States Patent
Ivarie et al.

(10) Patent No.: US 7,338,654 B2
(45) Date of Patent: *Mar. 4, 2008

(54) GLYCOSYLATED INTERFERON ALPHA OBTAINED FROM A TRANSGENIC CHICKEN

(75) Inventors: Robert D. Ivarie, Watkinsville, GA (US); Alex J. Harvey, Athens, GA (US); Julie A. Morris, Watkinsville, GA (US); Guodong Liu, Mississagua (CA); Jeffrey C. Rapp, Athens, GA (US)

(73) Assignees: AviGenics, Inc., Athens, GA (US); University of Georgia Research Foundation, Inc., Athens, GA (US)

( * ) Notice: Subject to any disclaimer, the term of this patent is extended or adjusted under 35 U.S.C. 154(b) by 97 days.

This patent is subject to a terminal disclaimer.

(21) Appl. No.: 11/370,555

(22) Filed: Mar. 8, 2006

(65) Prior Publication Data

US 2006/0171921 A1  Aug. 3, 2006

Related U.S. Application Data

(63) Continuation of application No. 10/351,196, filed on Jan. 24, 2003, now Pat. No. 7,129,390, which is a continuation-in-part of application No. 09/173,864, filed on Oct. 16, 1998, now Pat. No. 6,730,822.

(60) Provisional application No. 60/062,172, filed on Oct. 16, 1997.

(51) Int. Cl.
*A61K 38/21* (2006.01)

(52) U.S. Cl. ........... 424/85.5; 424/85.7; 530/351

(58) Field of Classification Search ........... None
See application file for complete search history.

(56) References Cited

U.S. PATENT DOCUMENTS

| | | | |
|---|---|---|---|
| 4,296,134 A | 10/1981 | Boldt | |
| 4,496,537 A | 1/1985 | Kwan | |
| 4,903,635 A | 2/1990 | Hebrank | |
| 4,959,317 A | 9/1990 | Sauer | |
| 4,997,763 A | 3/1991 | Hughes et al. | |
| 5,011,780 A | 4/1991 | Perry | |
| 5,056,464 A | 10/1991 | Lewis | |
| 5,162,215 A | 11/1992 | Bosselman et al. | |
| 5,304,489 A | 4/1994 | Rosen | |
| 5,354,674 A | 10/1994 | Hodgson | |
| 5,364,783 A | 11/1994 | Ruley et al. | |
| 5,367,054 A | 11/1994 | Lee | |
| 5,378,618 A | 1/1995 | Sternberg et al. | |
| 5,464,764 A | 11/1995 | Capecchi et al. | |
| 5,487,992 A | 1/1996 | Capecchi et al. | |
| 5,677,177 A | 10/1997 | Wahl et al. | |
| 5,714,353 A | 2/1998 | Pathak et al. | |
| 5,741,957 A | 4/1998 | Deboer et al. | |
| 5,784,992 A | 7/1998 | Petitte et al. | |
| 5,879,933 A | 3/1999 | Hodgson | |
| 5,885,567 A | 3/1999 | Sekellick et al. | |
| 5,897,998 A | 4/1999 | Speksnijder et al. | |
| 6,027,722 A | 2/2000 | Hodgson | |
| 6,069,133 A | 5/2000 | Chiou et al. | |
| 6,287,863 B1 | 9/2001 | Hodgson | |
| 6,410,220 B1 | 6/2002 | Hodgson et al. | |
| 6,825,396 B2 | 11/2004 | MacArthur | |
| 2002/0028488 A1 | 3/2002 | Singh et al. | |
| 2003/0172387 A1 | 9/2003 | Zhu et al. | |

FOREIGN PATENT DOCUMENTS

WO  WO 03/081993 A2  10/2003

OTHER PUBLICATIONS

Bosselman et al., Replication-Defective Vectors of Reticuloendotheliosis Virus Transduce Exogenous Genes . . . , Journal of Virology, 2680-2689 (1989).
Gibbins, Gene Constructs for Testing Transgenic Poultry, The Thirty-Seventh Annual National Breeders' Roundtable (1988).
Harvey et al., Expression of exogenous protein in the egg white of transgenic chickens, Nature Biotechnology, 19:396-99 (2002).
Shuman, Production of transgenic birds, Experientia 47, 897-905 (1991).
Zhu et al., Production of human monoclonal antibody in eggs of chimeric chickens, Nature Biotechnology, 23:(9)1159-69 (2005).

*Primary Examiner*—Robert S. Landsman
*Assistant Examiner*—Gyan Chandra
(74) *Attorney, Agent, or Firm*—Kyle D. Yesland

(57) ABSTRACT

This invention includes compositions comprising glycosylated human interferon-α derived from a chicken.

18 Claims, 18 Drawing Sheets

Figure 2
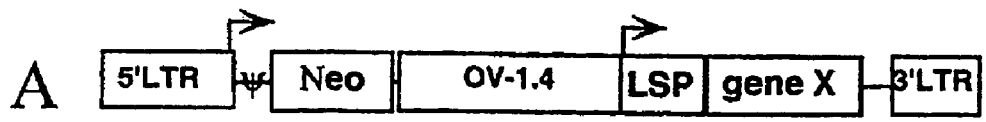
A
⎯▷ transcription start site
5' & 3' LTR: ALV long terminal repeats
Ψ virus packaging signal
Neo: neomycin-reistance gene
OV-1.4: ovalbumin -1.4 kb promoter
LSP: lysozyme signal peptide
gene X: gene or cDNA encoding an exogenous protein
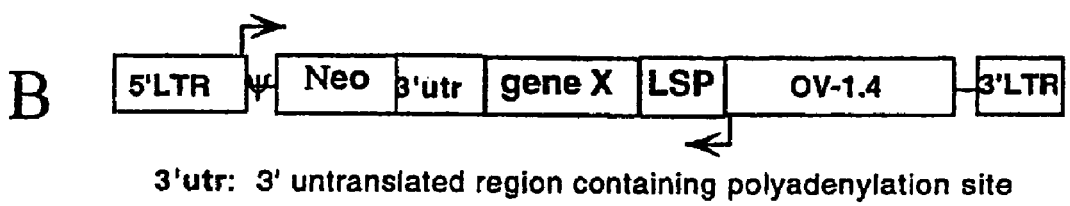
B
3'utr: 3' untranslated region containing polyadenylation site
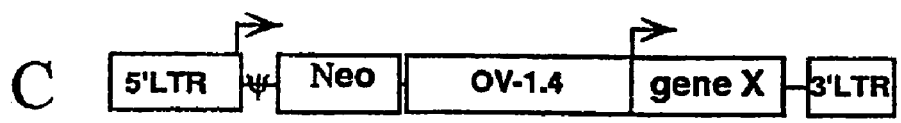
C
Same vector as A lacking LSP element
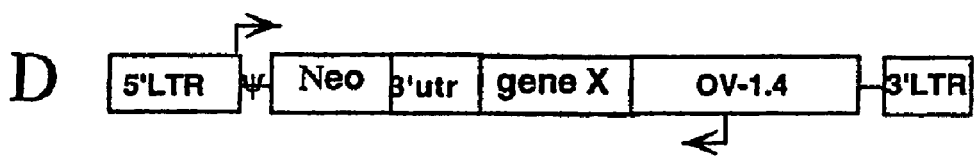
D
Same vector as B lacking LSP element

Figure 2E
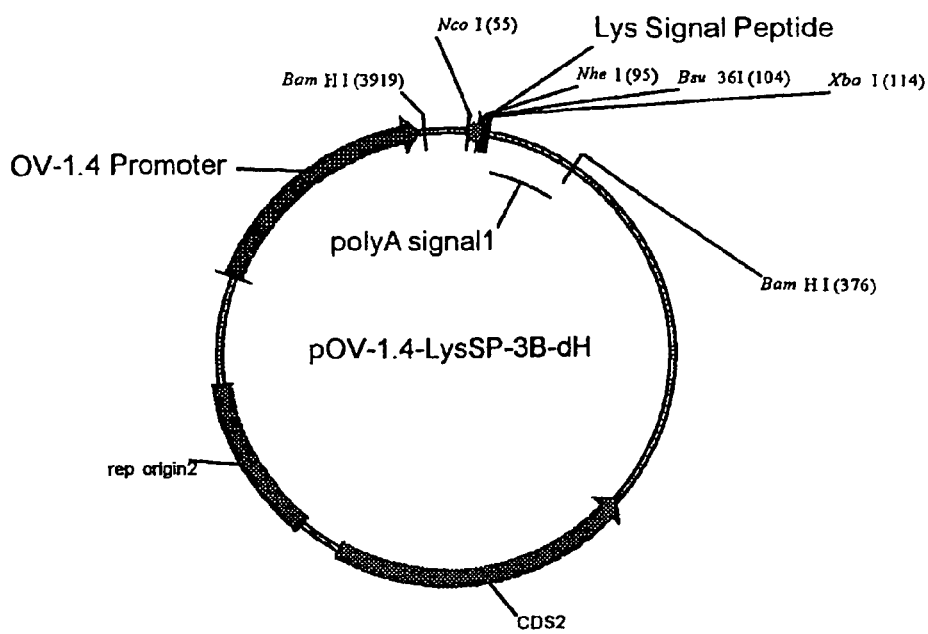
Lysozyme Signal Peptide
```
              M   G   S   L   L   I   L   V   L   C   F   L   P   L   A
         NcoI                                                      NheI
    51   CCACCATGGG GTCTTTGCTA ATCTTGGTGC TTTGCTTCCT GCCGCTAGCT
         GGTGGTACCC CAGAAACGAT TAGAACCACG AAACGAAGGA CGGCGATCGA
         A   L   G▼
         Bsu36I       XbaI              ▼ : Signal peptide cleavage site.
   101   GCCTTAGGGC CCTCTAGAG
         CGGAATCCCG GGAGATCTC
```
PCR Cloning of cDNA
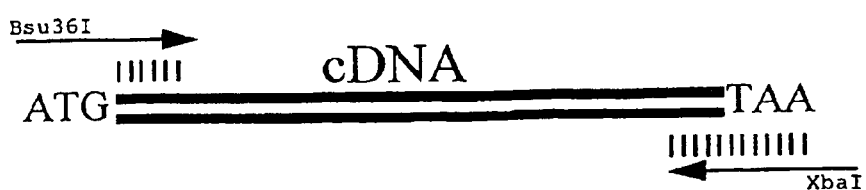

↱ transcription start site
5' & 3' LTR: ALV long terminal repeats
Ψ virus packaging signal
Neo: neomycin-reistance gene
OV - 1.4: ovalbumin -1.4 kb promoter
LSP: lysozyme signal peptide
gene X: gene or cDNA encoding an exogenous protein
gene Y: gene or cDNA encoding an exogenous protein
IRES: internal ribosome entry site

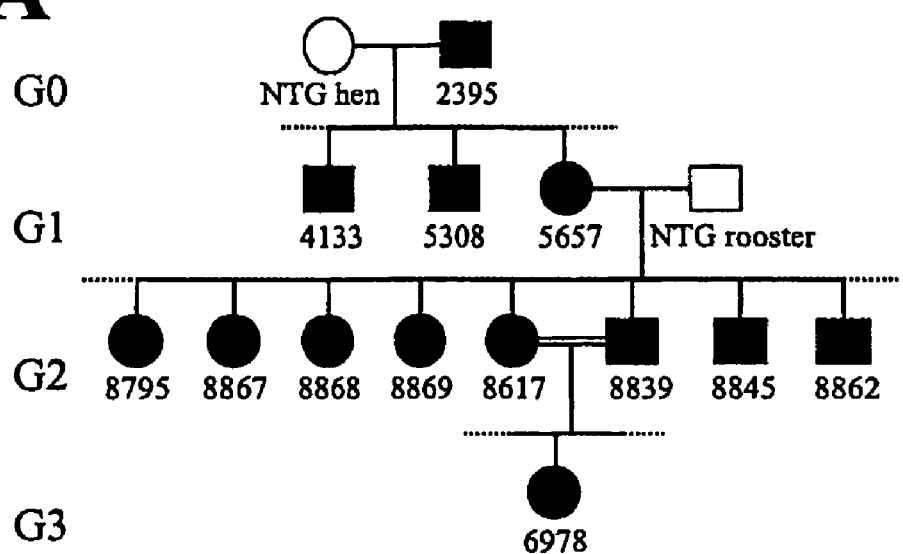
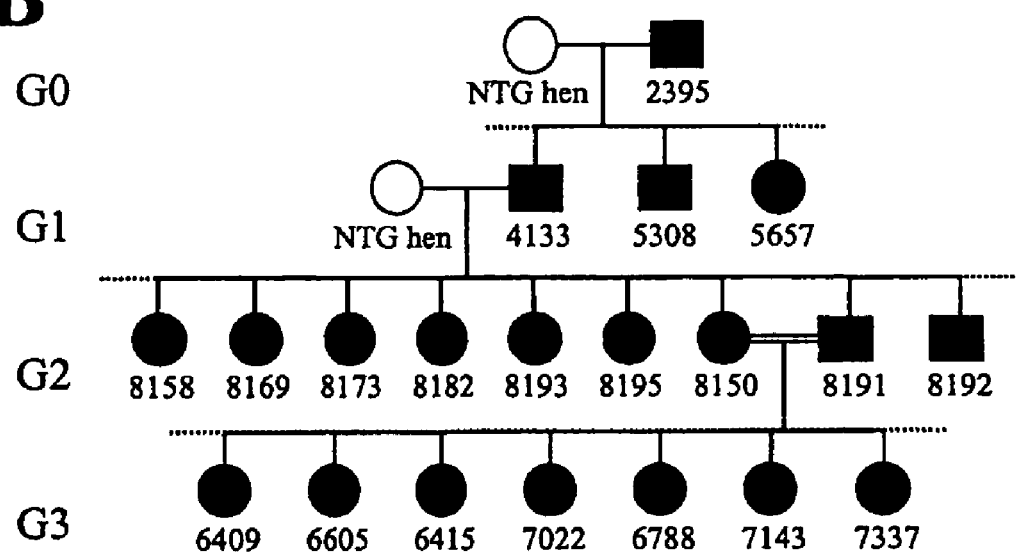
Figure 5

Figure 11

CDLPQTHSLGSRRTLMLLAQMRRISLFSCLKDRHDFGFPQEEFGNQFQKAETIPVLHE
MIQQIFNLFSTKDSSAAWDETLLDKFYTELYQQLNDLEACVIQGVGVTETPLMKEDS
ILAVRKYFQRITLYLKEKKYSPCAWEVVRAEIMRSFSLSTNLQESLRSKE

ATGGGCGTGCACGAGTGCCCTGCTTGGCTGTGGCTGCTCTTGAGCCTGCTCAGCC
TGCCTCTGGGCCTGCCTGTGCTGGGCGCTCCTCCAAGGCTGATCTGCGATAGCAG
GGTGCTGGAGAGGTACCTGCTGGAGGCTAAGGAGGCTGAGAACATCACCACCGG
CTGCGCTGAGCACTGCAGCCTGAACGAGAACATCACCGTGCCTGATACCAAGGT
GAACTTTTACGCTTGGAAGAGGATGGAGGTGGGCCAGCAGGCTGTGGAGGTGTG
GCAGGGCCTGGCTCTGCTGAGCGAGGCTGTGCTGAGGGGCCAGGCTCTGCTGGT
GAACAGCTCTCAGCCTTGGGAGCCTCTGCAGCTGCACGTGGATAAGGCTGTGAG
CGGCCTGAGAAGCCTGACCACCCTGCTGAGGGCTCTGGGCGCTCAGAAGGAGGC
TATCAGCCCTCCAGATGCTGCAAGCGCTGCCCCTCTGAGGACCATCACCGCTGAT
ACCTTTAGGAAGCTGTTTAGGGTGTACAGCAACTTTCTGAGGGGCAAGCTGAAG
CTGTACACCGGCGAGGCTTGCAGGACCGGCGATAGG

B

MGVHECPAWLWLLLSLLSLPLGLPVLGAPPRLICDSRVLERYLLEAKEAENITTGCA
EHCSLNENITVPDTKVNFYAWKRMEVGQQAVEVWQGLALLSEAVLRGQALLVNSS
QPWEPLQLHVDKAVSGLRSLTTLLRALRAQKEAISPPDAASAAPLRTITADTFRKLFR
VYSNFLRGKLKLYTGEACRTGDR

Figure 13
MDOT Promoter

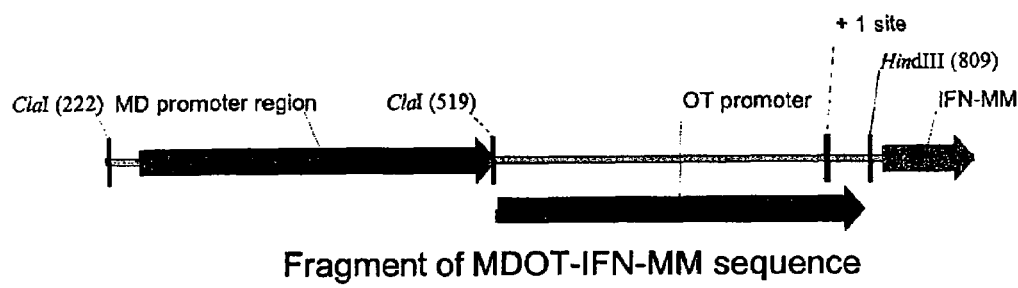

Fragment of MDOT-IFN-MM sequence

```
        ClaI
        ------
220 ATCGATAGGT ACCGGGCCCC CCCTCGAGGT GAATATCCAA GAATGCAGAA CTGCATGGAA AGCAGAGCTG
290 CAGGCACGAT GGTGCTGAGC CTTAGCTGCT TCCTGCTGGG AGATGTGGAT GCAGAGACGA ATGAAGGACC
360 TGTCCCTTAC TCCCCTCAGC ATTCTGTGCT ATTTAGGGTT CTACCAGAGT CCTTAAGAGG TTTTTTTTTT
430 TTTTGGTCCA AAAGTCTGTT TGTTTGGTTT TGACCACTGA GAGCATGTGA CACTTGTCTC AAGCTATTAA
                    ClaI
                    ------
500 CCAAGTGTCC AGCCAAAATC GATGTCACAA CTTGGGAATT TTCCATTTGA AGCCCCTTGC AAAAACAAAG
570 AGCACCTTGC CTGCTCCAGC TCCTGGCTGT GAAGGGTTTT GGTGCCAAAG AGTGAAAGGC TTCCTAAAAA
640 TGGGCTGAGC CGGGGAAGGG GGGCAACTTG GGGGCTATTG AGAAACAAGG AAGGACAAAC AGCGTTAGGT
710 CATTGCTTCT GCAAACACAG CCAGGGCTGC TCCTCTATAA AAGGGGAAGA AAGAGGCTCC GCAGCCATCA
                              HindIII
                              -------
                                          Met AlaLeuThr PheAlaLeu LeuValAlaLeu
780 CAGACCCAGA GGGGACGGTC TGTGAATCAA GCTTTCACCA TGGCTTTGAC CTTTGCCTTA CTGGTGGCTC
       LLeuValLeu SerCysLys SerSerCysSer TrpValAla
850 TCCTGGTGCT GAGCTGCAAG AGCAGCTGCT CGTGGGTTGC G
```

Figure 14
Summary of Major Egg White Proteins

| Gene | Expression | Amount in Albumin (%) | mg of Protein per Egg | MW kDa | Molar Concentr (mM) | Promoter Cloned: |
|---|---|---|---|---|---|---|
| ovalbumin | magnum | 63 | 2520 | 43 | 1.628 | yes |
| ovomucoid | magnum | 11 | 440 | 28 | 0.437 | 0.438 kb available |
| ovotransferrin | magnum liver | 12 | 480 | 80 | 0.167 | 1.1 kb available |
| lysozyme | magnum macrophages | 3.4 | 136 | 14 | 0.270 | yes |
| ovomucin | magnum | 3.5 / 2 | 140 / 80 | 700 / 700 | 0.006 / 0.003 | no |
| ovoinhibitor | magnum liver | 1.4 / 1 mg/ml in | 56 | 46.5 | 0.033 | gene sequence is known |

A.
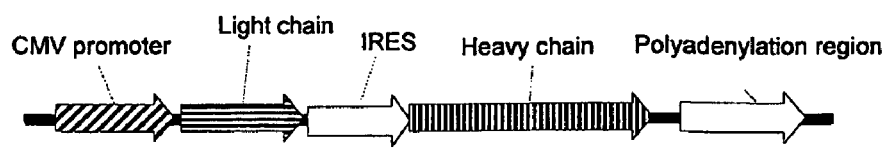
B.
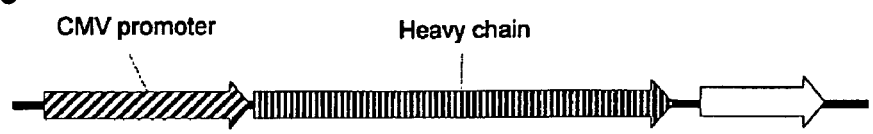
C.
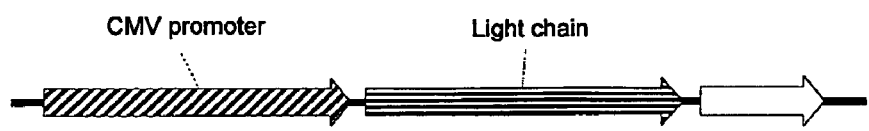
D.
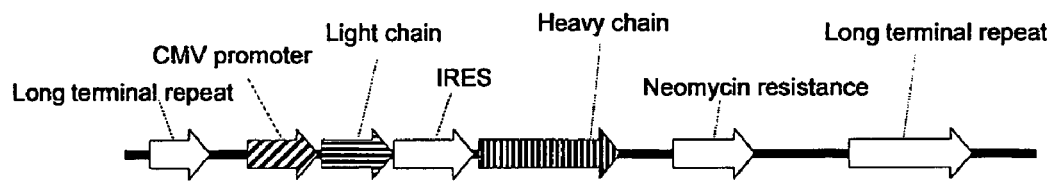
Figure 15

GLYCOSYLATED INTERFERON ALPHA OBTAINED FROM A TRANSGENIC CHICKEN

This application is a continuation of U.S. application Ser. No. 10/351,196, filed Jan. 24, 2003, now U.S. Pat. No. 7,129,390, issued Oct. 31, 2006, the disclosure of which is incorporated in its entirety herein by reference, which is a continuation-in-part of U.S. application Ser. No. 09/173,864, filed Oct. 16, 1998, the disclosure of which is incorporated in its entirety herein by reference, now U.S. Pat. No. 6,730,822, issued May 4, 2004, which claims priority from U.S. provisional application No. 60/062,172, filed Oct. 16, 1997.

BACKGROUND OF THE INVENTION a) Field of the Invention

The present invention relates to vectors and methods for the introduction of exogenous genetic material into avian cells and the expression of the exogenous genetic material in the cells. The invention also relates to transgenic avian species, including chicken and turkey, and to avian eggs which contain exogenous protein.

b) Description of Related Art

Numerous natural and synthetic proteins are used in diagnostic and therapeutic applications; many others are in development or in clinical trials. Current methods of protein production include isolation from natural sources and recombinant production in bacterial and mammalian cells. Because of the complexity and high cost of these methods of protein production, however, efforts are underway to develop alternatives. For example, methods for producing exogenous proteins in the milk of pigs, sheep, goats, and cows have been reported. These approaches suffer from several limitations, including long generation times between founder and production transgenic herds, extensive husbandry and veterinary costs, and variable levels of expression because of position effects at the site of the transgene insertion in the genome. Proteins are also being produced using milling and malting processes from barley and rye. However, plant post-translational modifications differ from vertebrate post-translational modifications, which often has a critical effect on the function of the exogenous proteins.

The Oviduct as a Bioreactor

Like tissue culture and mammary gland bioreactors, the avian oviduct can also potentially serve as a bioreactor. Successful methods of modifying avian genetic material such that high levels of exogenous proteins are secreted in and packaged into eggs would allow inexpensive production of large amounts of protein. Several advantages of such an approach would be: a) short generation times (24 weeks) and rapid establishment of transgenic flocks via artificial insemination; b) readily scaled production by increasing flock sizes to meet production needs; c) post-translational modification of expressed proteins; d) automated feeding and egg collection; e) naturally sterile egg-whites; and f) reduced processing costs due to the high concentration of protein in the egg white.

The avian reproductive system, including that of the chicken, is well described. The egg of the hen consists of several layers which are secreted upon the yolk during its passage through the oviduct. The production of an egg begins with formation of the large yolk in the ovary of the hen. The unfertilized oocyte is then positioned on top of the yolk sac. Upon ovulation or release of the yolk from the ovary, the oocyte passes into the infundibulum of the oviduct where it is fertilized if sperm are present. It then moves into the magnum of the oviduct which is lined with tubular gland cells. These cells secrete the egg-white proteins, including ovalbumin, lysozyme, ovomucoid, conalbumin, and ovomucin, into the lumen of the magnum where they are deposited onto the avian embryo and yolk.

The ovalbumin gene encodes a 45 kD protein that is specifically expressed in the tubular gland cells of the magnum of the oviduct (Beato, *Cell* 56:335-344 (1989)). Ovalbumin is the most abundant egg white protein, comprising over 50 percent of the total protein produced by the tubular gland cells, or about 4 grams of protein per large Grade A egg (Gilbert, "Egg albumen and its formation" in *Physiology and Biochemistry of the Domestic Fowl*, Bell and Freeman, eds., Academic Press, London, New York, pp. 1291-1329). The ovalbumin gene and over 20 kb of each flanking region have been cloned and analyzed (Lai et al., *Proc. Natl. Acad. Sci. USA* 75:2205-2209 (1978); Gannon et al., *Nature* 278:428-424 (1979); Roop et al., *Cell* 19:63-68 (1980); and Royal et al., *Nature* 279:125-132 (1975)).

Much attention has been paid to the regulation of the ovalbumin gene. The gene responds to steroid hormones such as estrogen, glucocorticoids, and progesterone, which induce the accumulation of about 70,000 ovalbumin mRNA transcripts per tubular gland cell in immature chicks and 100,000 ovalbumin mRNA transcripts per tubular gland cell in the mature laying hen (Palmiter, *J. Biol. Chem.* 248:8260-8270 (1973); Palmiter, *Cell* 4:189-197 (1975)). DNAse hypersensitivity analysis and promoter-reporter gene assays in transfected tubular gland cells defined a 7.4 kb region as containing sequences required for ovalbumin gene expression. This 5' flanking region contains four DNAse I-hypersensitive sites centered at −0.25, −0.8, −3.2, and −6.0 kb from the transcription start site. These sites are called HS-I, -II, -III, and -IV, respectively. These regions reflect alterations in the chromatin structure and are specifically correlated with ovalbumin gene expression in oviduct cells (Kaye et al., *EMBO* 3:1137-1144 (1984)). Hypersensitivity of HS-II and -III are estrogen-induced, supporting a role for these regions in hormone-induction of ovalbumin gene expression.

HS-I and HS-II are both required for steroid induction of ovalbumin gene transcription, and a 1.4 kb portion of the 5' region that includes these elements is sufficient to drive steroid-dependent ovalbumin expression in explanted tubular gland cells (Sanders and McKnight, *Biochemistry* 27:6550-6557 (1988)). HS-I is termed the negative-response element ("NRE") because it contains several negative regulatory elements which repress ovalbumin expression in the absence of hormones (Haekers et al., *Mol. Endo.* 9:1113-1126 (1995)). Protein factors bind these elements, including some factors only found in oviduct nuclei suggesting a role in tissue-specific expression. HS-II is termed the steroid-dependent response element ("SDRE") because it is required to promote steroid induction of transcription. It binds a protein or protein complex known as Chirp-I. Chirp-I is induced by estrogen and turns over rapidly in the presence of cyclohexamide (Dean et al., *Mol. Cell. Biol.* 16:2015-2024 (1996)). Experiments using an explanted tubular gland cell culture system defined an additional set of factors that bind SDRE in a steroid-dependent manner, including a NFκB-like factor (Nordstrom et al., *J. Biol. Chem.* 268:13193-13202 (1993); Schweers and Sanders, *J. Biol. Chem.* 266: 10490-10497 (1991)).

Less is known about the function of HS-III and -IV. HS-III contains a functional estrogen response element, and confers estrogen inducibility to either the ovalbumin proximal promoter or a heterologous promoter when co-transfected into HeLa cells with an estrogen receptor cDNA. These data imply that HS-III may play a functional role in the overall regulation of the ovalbumin gene. Little is known about the function of HS-IV, except that it does not contain a functional estrogen-response element (Kato et al., *Cell* 68: 731-742 (1992)).

There has been much interest in modifying eukaryotic genomes by introducing foreign genetic material and/or by disrupting specific genes. Certain eukaryotic cells may prove to be superior hosts for the production of exogenous eukaryotic proteins. The introduction of genes encoding certain proteins also allows for the creation of new phenotypes which could have increased economic value. In addition, some genetically-caused disease states may be cured by the introduction of a foreign gene that allows the genetically defective cells to express the protein that it can otherwise not produce. Finally, modification of animal genomes by insertion or removal of genetic material permits basic studies of gene function, and ultimately may permit the introduction of genes that could be used to cure disease states, or result in improved animal phenotypes.

Transgenic Animals

Transgenesis has been accomplished in mammals by several different methods. First, in mammals including the mouse, pig, goat, sheep and cow, a transgene is microinjected into the pronucleus of a fertilized egg, which is then placed in the uterus of a foster mother where it gives rise to a founder animal carrying the transgene in its germline. The transgene is engineered to carry a promoter with specific regulatory sequences directing the expression of the foreign protein to a particular cell type. Since the transgene inserts randomly into the genome, position effects at the site of the transgene's insertion into the genome may variably cause decreased levels of transgene expression. This approach also requires characterization of the promoter such that sequences necessary to direct expression of the transgene in the desired cell type are defined and included in the transgene vector (Hogan et al. *Manipulating the Mouse Embryo*, Cold Spring Harbor Laboratory, NY (1988)).

A second method for effecting animal transgenesis is targeted gene disruption, in which a targeting vector bearing sequences of the target gene flanking a selectable marker gene is introduced into embryonic stem ("ES") cells. Via homologous recombination, the targeting vector replaces the target gene sequences at the chromosomal locus or inserts into interior sequences preventing expression of the target gene product. Clones of ES cells bearing the appropriately disrupted gene are selected and then injected into early stage blastocysts generating chimeric founder animals, some of which bear the transgene in the germ line. In the case where the transgene deletes the target locus, it replaces the target locus with foreign DNA borne in the transgene vector, which consists of DNA encoding a selectable marker useful for detecting transfected ES cells in culture and may additionally contain DNA sequences encoding a foreign protein which is then inserted in place of the deleted gene such that the target gene promoter drives expression of the foreign gene (U.S. Pat. Nos. 5,464,764 and 5,487,992 (M. P. Capecchi and K. R. Thomas)). This approach suffers from the limitation that ES cells are unavailable in many mammals, including goats, cows, sheep and pigs. Furthermore, this method is not useful when the deleted gene is required for survival or proper development of the organism or cell type.

Recent developments in avian transgenesis have allowed the modification of avian genomes. Germ-line transgenic chickens may be produced by injecting replication-defective retrovirus into the subgerminal cavity of chick blastoderms in freshly laid eggs (U.S. Pat. No. 5,162,215; Bosselman et al., *Science* 243:533-534 (1989); Thoraval et al., *Transgenic Research* 4:369-36 (1995)). The retroviral nucleic acid carrying a foreign gene randomly inserts into a chromosome of the embryonic cells, generating transgenic animals, some of which bear the transgene in their germ line. Use, of insulator elements inserted at the 5' or 3' region of the fused gene construct to overcome position effects at the site of insertion has been described (Chim et al., *Cell* 74:504-514 (1993)).

In another approach, a transgene has been microinjected into the germinal disc of a fertilized egg to produce a stable transgenic founder avian that passes the gene to the F1 generation (Love et al. *Bio/Technology* 12:60-63 (1994)). However, this method has several disadvantages. Hens must be sacrificed in order to collect the fertilized egg, the fraction of transgenic founders is low, and injected eggs require labor intensive in vitro culture in surrogate shells.

In another approach, blastodermal cells containing presumptive primordial germ cells ("PGCs") are excised from donor eggs, transfected with a transgene and introduced into the subgerminal cavity of recipient embryos. The transfected donor cells are incorporated into the recipient embryos generating transgenic embryos, some of which are expected to bear the transgene in the germ line. The transgene inserts in random chromosomal sites by nonhomologous recombination. However, no transgenic founder avians have yet been generated by this method.

Lui, *Poult. Sci.* 68:999-1010 (1995), used a targeting vector containing flanking DNA sequences of the vitellogenin gene to delete part of the resident gene in chicken blastodermal cells in culture. However, it has not been demonstrated that these cells can contribute to the germ line and thus produce a transgenic embryo. In addition, this method is not useful when the deleted gene is required for survival or proper development of the organism or cell type.

Thus, it can be seen that there is a need for a method of introducing foreign DNA, operably linked to a suitable promoter, into the avian genome such that efficient expression of an exogenous gene can be achieved. Furthermore, there exists a need to create germ-line modified transgenic avians which express exogenous genes in their oviducts and secrete the expressed exogenous proteins into their eggs.

Interferon

When interferon was discovered in 1957, it was hailed as a significant antiviral agent. In the late 1970s, interferon became associated with recombinant gene technology. Today, interferon is a symbol of the complexity of the biological processes of cancer and the value of endurance and persistence in tackling this complexity.

The abnormal genes that cause cancer comprise at least three types: Firstly, there are the oncogenes, which, when altered, encourage the abnormal growth and division that characterize cancer. Secondly, there are the tumor suppressor genes, which, when altered, fail to control this abnormal growth and division. Thirdly, there are the DNA repair genes, which, when altered, fail to repair mutations that can lead to cancer. Researchers speculate that there are about 30 to 40 tumor suppressor genes in the body, each of which produces a protein. These proteins may be controlled by "master" tumor suppressor proteins such as Rb (for retinoblastoma, with which it was first associated) and p53 (associated with many different tumors). Evidence from the laboratory suggests that returning just one of these tumor suppressor genes to its normal function can appreciably reduce the aggressiveness of the malignancy.

Scientists became intrigued by interferon when it was discovered that interferon can inhibit cell growth. Further, interferon was found to have certain positive effects on the immune system. It is now considered analogous to a tumor suppressor protein: it inhibits the growth of cells, particularly malignant cells; it blocks the effects of many oncogenes and growth factors; and unlike other biological agents, it inhibits cell motility which is critical to the process of metastasis.

Intercellular communication is dependent on the proper functioning of all the structural components of the tissue through which the messages are conveyed: the matrix, the cell membrane, the cytoskeleton, and the cell itself. In cancer, the communication network between cells is disrupted. If the cytoskeleton is disrupted, the messages don't get through to the nucleus and the nucleus begins to function abnormally. Since the nucleus is the site where the oncogenes or tumor suppressor genes get switched on or off, this abnormal functioning can lead to malignancy. When this happens, the cells start growing irregularly and do not differentiate. They may also start to move and disrupt other cells. It is believed that interferon, probably in concert with other extracellular and cellular substances, restores the balance and homeostasis, making sure the messages get through properly. Interferon stops growth, stops motility, and enhances the ability of the cell, through adhesion molecules, to respond to its environment. It also corrects defects and injuries in the cytoskeleton. Interferon has been found to block angiogenesis, the initial step in the formation of new blood vessels that is essential to the growth of malignancies. Moreover, it blocks fibrosis, a response to injury that stimulates many different kinds of cells and promotes cell growth (Kathryn L. Hale, *Oncolog*, Interferon: The Evolution of a Biological Therapy, Taking a New Look at Cytokine Biology).

Interferon is produced by animal cells when they are invaded by viruses and is released into the bloodstream or intercellular fluid to induce healthy cells to manufacture an enzyme that counters the infection. For many years the supply of human interferon for research was limited by costly extraction techniques. In 1980, however, the protein became available in greater quantities through genetic engineering (i.e., recombinant forms of the protein). Scientists also determined that the body makes three distinct types of interferon, referred to as α-(alpha), β-(beta), and γ-(gamma) interferon. Interferons were first thought to be highly species-specific, but it is now known that individual interferons may have different ranges of activity in other species. Alpha interferon (α-IFN) has been approved for therapeutic use against hairy-cell leukemia and hepatitis C. α-IFN has also been found effective against chronic hepatitis B, a major cause of liver cancer and cirrhosis, as well as for treatment of genital warts and some rarer cancers of blood and bone marrow. Nasal sprays containing α-IFN provide some protection against colds caused by rhinoviruses. Human α-IFN belongs to a family of extra-cellular signaling proteins with antiviral, antiproliferating and immunomodulatory activities. IFN-α proteins are encoded by a multigene family which includes 13 genes clustered on the human chromosome 9. Most of the IFN-α genes are expressed at the mRNA level in leukocytes induced by Sendai virus. Further, it has been shown that at least nine different sub-types are also produced at the protein level. The biological significance of the expression of several similar IFN-α proteins is not known, however, it is believed that they have quantitatively distinct patterns of antiviral, growth inhibitory and killer-cell-stimulatory activities. Currently, two IFN-α variants, IFN-α 2a and IFN-α 2b, are mass produced in *Escherichia coli* by recombinant technology and marketed as drugs. Unlike natural IFN-α, these recombinant IFN-α products have been shown to be immunogenic in some patients, which could be due to unnatural forms of IFN-α proteins. Thus, for the development of IFN-α drugs it is necessary to not only identify the IFN-α subtypes and variants expressed in normal human leukocytes, but also to characterize their possible post-translational modifications (Nyman et al. (1998) *Eur. J. Biochem.* 253:485-493).

Nyman et al. (supra) studied the glycosylation of natural human IFN-α. They found that two out of nine of the subtypes produced by leukocytes after a Sendai-virus induction were found to be glycosylated, namely IFN-α 14c and IFN-α 2b, which is consistent with earlier studies. IFN-α 14 is the only IFN-α subtype with potential N-glycosylation sites, Asn2 and Asn72, but only Asn72 is actually glycosylated. IFN-α 2 is O-glycosylated at Threonine 106 (Thr106). Interestingly, no other IFN-α subtype contains Thr at this position. In this study, Nyman et al. liberated and isolated the oligosaccharide chains and analyzed their structures by mass spectrometry and specific glycosidase digestions. Both IFN-α 2b and IFN-α 14c resolved into three peaks in reversed-phase high performance liquid chromatography (RP-HPLC). Electrospray ionization mass spectrometry (ESI-MS) analysis of IFN-α 2b fractions from RP-HPLC revealed differences in their molecular masses, suggesting that these represent different glycoforms. This was confirmed by masspectrometric analysis of the liberated O-glycans of each fraction. IFN-α 2b was estimated to contain about 20% of the core type-2 pentasaccharide, and about 50% of disialylated and 30% of monosialylated core type-1 glycans. Nyman et al.'s data agrees with previous partial characterization of IFN-α 2b glycosylation (Adolf et al. (1991) *Biochem. J.* 276:511-518). The role of glycosylation in IFN-α 14c and IFN-α 2b is not clearly established. According to Nyman et al. (supra), the carbohydrate chains are not essential for the biological activity, but glycosylation may have an effect on the pharmacokinetics and stability of the proteins.

There are at least 15 functional genes in the human genome that code for proteins of the IFN-α family. The amino acid sequence similarities are generally in the region of about 90%, thus, these molecules are closely related in structure. IFN-α proteins contain 166 amino acids (with the exception of IFN-α 2, which has 165 amino acids) and characteristically contain four conserved cysteine residues which form two disulfide bridges. IFN-α species are slightly acidic in character and lack a recognition site for asparagine-linked glycosylation (with the exception of IFN-α 14 which does contain a recognition site for asparagine-linked glycosylation). Three variants of IFN-α 2, differing in their amino acids at positions 23 and 34, are known: IFN-α 2a (Lys-23, His-34); IFN-α 2b (Arg-23, His-34); and IFN-α 2c (Arg-23, Arg-34). Two other human IFN species, namely IFN-ω1 and IFN-β are N-glycosylated and are more distantly related to IFN-α. IFN-α, -β and -ω, collectively referred to as class I IFNs, bind to the same high affinity cell membrane receptor (Adolf et al. (1991) *Biochem. J.* 276:511-518).

Adolf et al. (supra) used the specificity of a monoclonal antibody for the isolation of natural IFN-α 2 from human leukocyte IFN. They obtained a 95% pure protein through immunoaffinity chromatography which confirmed the expected antiviral activity of IFN-α 2. Analysis of natural IFN-α 2 by reverse-phase HPLC, showed that the natural protein can be resolved into two components, both more hydrophilic than *E. coli*-derived IFN-α 2. SDS/PAGE revealed that the protein is also heterogeneous in molecular mass, resulting in three bands, all of them with lower electrophoretic mobility than the equivalent *E. coli*-derived protein.

Adolf et al. (supra) also speculated that natural IFN-α 2 carries O-linked carbohydrate residues. Their hypothesis was confirmed by cleavage of the putative peptide-carbohydrate bond with alkali; the resulting protein was homogeneous and showed the same molecular mass as the recombinant protein. Further comparison of natural and recombinant proteins after proteolytic cleavage, followed by separation and analysis of the resulting fragments, allowed them to define a candidate glycopeptide. Sequence analysis of this peptide identified Thr-106 as the O-glycosylation site. A comparison of the amino acid sequences of all published IFN-α 2 species revealed that this threonine residue is unique to IFN-α 2. Glycine, isoleucine or glutamic acid are present at the corresponding position (107) in all other proteins.

Preparations of IFN-α 2 produced in *E. coli* are devoid of O-glycosylation and have been registered as drugs in many countries. However, the immunogenicity of therapeutically applied *E. coli*-derived IFN-α 2 might be affected by the lack of glycosylation. Studies have shown that four out of sixteen patients receiving recombinant human granulocyte-macrophage colony-stimulating factor produced in yeast developed antibodies to this protein. Interestingly, these antibodies were found to react with epitopes that in the endogenous granulocyte-macrophage colony-stimulating factor are protected by O-linked glycosylation, but which are exposed in the recombinant factor (Adolf et al., supra).

Similarly, induction of antibodies to recombinant *E. coli*-derived IFN-α 2 after prolonged treatment of patients has been described and it has been speculated that natural IFN-α 2 may be less immunogenic than the recombinant IFN-α 2 proteins (Galton et al. (1989) Lancet 2:572-573).

SUMMARY OF THE INVENTION

This invention provides vectors and methods for the stable introduction of exogenous nucleic acid sequences into the genome of avians in order to express the exogenous sequences to alter the phenotype of the avians or to produce desired proteins. In particular, transgenic avians are produced which express exogenous sequences in their oviducts and which deposit exogenous proteins into their eggs. Avian eggs that contain exogenous proteins are encompassed by this invention. The instant invention further provides novel forms of interferon and erythropoietin which are efficiently expressed in the oviduct of transgenic avians and deposited into avian eggs.

One aspect of the present invention provides methods for producing exogenous proteins in specific tissues of avians. Exogenous proteins may be expressed in the oviduct, blood and/or other cells and tissues of the avian. Transgenes are introduced into embryonic blastodermal cells, preferably near stage X, to produce a transgenic avian, such that the protein of interest is expressed in the tubular gland cells of the magnum of the oviduct, secreted into the lumen, and deposited into the egg white of a hard shell egg. A transgenic avian so produced carries the transgene in its germ line. The exogenous genes can therefore be transmitted to avians by both artificial introduction of the exogenous gene into avian embryonic cells, and by the transmission of the exogenous gene to the avian's offspring stably in a Mendelian fashion.

The present invention encompasses a method of producing an exogenous protein in an avian oviduct. The method comprises as a first step providing a vector that contains a coding sequence and a promoter operably linked to the coding sequence, so that the promoter can effect expression of the nucleic acid in the avian oviduct. Next, transgenic cells and/or tissues are created, wherein the vector is introduced into avian embryonic blastodermal cells, either freshly isolated, in culture, or in an embryo, so that the vector sequence is randomly inserted into the avian genome. Finally, a mature transgenic avian which expresses the exogenous protein in its oviduct is derived from the transgenic cells and/or tissue. This method can also be used to produce an avian egg which contains exogenous protein when the exogenous protein that is expressed in the oviduct is also secreted into the oviduct lumen and deposited into the egg white of a hard shell egg.

In one aspect, the production of a transgenic bird by random chromosomal insertion of a vector into its avian genome may optionally involve DNA transfection of embryonic blastodermal cells which are then injected into the subgerminal cavity beneath a recipient blastoderm. The vector used in such a method has a promoter which is fused to an exogenous coding sequence and directs expression of the coding sequence in the tubular gland cells of the oviduct.

In another aspect of the invention, a random chromosomal insertion and the production of a transgenic avian is accomplished by transduction of embryonic blastodermal cells with replication-defective or replication-competent retroviral particles carrying the transgene genetic code between the 5' and 3' LTRs of the retroviral rector. For instance, an avian leukosis virus (ALV) retroviral vector or a murine leukemia virus (MLV) retroviral vector may be used which comprises a modified pNLB plasmid containing an exogenous gene that is inserted downstream of a segment of a promoter region. An RNA copy of the modified retroviral vector, packaged into viral particles, is used to infect embryonic blastoderms which develop into transgenic avians. Alternatively, helper cells which produce the retroviral transducing particles are delivered to the embryonic blastoderm.

Another aspect of the invention provides a vector which includes a coding sequence and a promoter in operational and positional relationship such that the coding sequence is expressed in an avian oviduct. The vector includes, but is not limited to, an avian leukosis virus (ALV) retroviral vector, a murine leukemia virus (MLV) retroviral vector, and a lentivirus vector. The promoter is sufficient for effecting expression of the coding sequence in the avian oviduct. The coding sequence codes for an exogenous protein which is deposited into the egg white of a hard shell egg. As such, the coding sequence codes for exogenous proteins such as transgenic poultry derived interferon-α 2b (TPD IFN-α 2b) or transgenic poultry derived erythropoietin (TPD EPO). The vector used in the methods of the invention contains a promoter which is particularly suited for expression of exogenous proteins in avians and their eggs. As such, expression of the exogenous coding sequence occurs in the oviduct and blood of the transgenic avian and in the egg white of its avian egg. The promoter includes, but is not limited to, a cytomegalovirus (CMV) promoter, a MDOT promoter, a rous-sarcoma virus (RSV) promoter, a murine leukemia virus (MLV) promoter, a mouse mammary tumor virus (MMTV) promoter, an ovalbumin promoter, a lysozyme promoter, a conalbumin promoter, an ovomucoid promoter, an ovomucin promoter, and an ovotransferrin promoter. Optionally, the promoter may be a segment of at least one promoter region, such as a segment of the ovalbumin-, lysozyme-, conalbumin-, ovomucoid-, ovomucin-, and ovotransferrin promoter region.

One aspect of the invention involves truncating the ovalbumin promoter and/or condensing the critical regulatory elements of the ovalbumin promoter so that it retains sequences required for expression in the tubular gland cells of the magnum of the oviduct, while being small enough that it can be readily incorporated into vectors. For instance, a segment of the ovalbumin promoter region may be used. This segment comprises the 5'-flanking region of the ovalbumin gene. The total length of the ovalbumin promoter segment may be from about 0.88 kb to about 7.4 kb in length, and is preferably from about 0.88 kb to about 1.4 kb in length. The segment preferably includes both the steroid-dependent regulatory element and the negative regulatory element of the ovalbumin gene. The segment optionally also includes residues from the 5'untranslated region (5'UTR) of the ovalbumin gene. Alternatively, the promoter may be a segment of the promoter region of the lysozyme-, conalbumin-, ovomucin-, ovomucoid- and ovotransferrin genes. An example of such a promoter is the synthetic MDOT promoter which is comprised of elements from the ovomucoid (MD) and ovotransferrin (OT) promoter.

In another aspect of the invention, the vectors integrated into the avian genome contain constitutive promoters which are operably linked to the exogenous coding sequence (e.g., cytomegalovirus (CMV) promoter, rous-sarcoma virus (RSV) promoter, and a murine leukemia virus (MLV) promoter. Alternatively, a non-constitutive promoter such as a mouse mammary tumor virus (MMTV) promoter may be used.

Other aspects of the invention provide for transgenic avians which carry a transgene in the genetic material of their germ-line tissue. More specifically, the transgene includes an exogenous gene and a promoter in operational and positional relationship to express the exogenous gene. The exogenous gene is expressed in the avian oviduct and in the blood of the transgenic avian. The exogenous gene codes for exogenous proteins such as TPD IFN-α 2b or TPD EPO. The exogenous protein is deposited into the egg white of a hard shell egg.

Another aspect of the invention provides for an avian egg which contains protein exogenous to the avian species. Use of the invention allows for expression of exogenous proteins in oviduct cells with secretion of the proteins into the lumen of the oviduct magnum and deposition into the egg white of the avian egg. Proteins packaged into eggs may be present in quantities of up to one gram or more per egg. The exogenous protein includes, but is not limited to, TPD IFN-α 2b and TPD EPO.

Still another aspect of the invention provides an isolated polynucleotide sequence comprising the optimized coding sequence of human interferon-α 2b (IFN-α 2b), i.e., recombinant transgenic poultry derived interferon-α 2b coding sequence which codes for transgenic poultry derived interferon-α 2b (TPD IFN-α 2b). The invention also encompasses an isolated protein comprising the polypeptide sequence of TPD IFN-α 2b, wherein the protein is O-glycosylated at Thr-106 with N-Acetyl-Galactosamine, Galactose, N-Acetyl-Glucosamine, Sialic acid, and combinations thereof.

The invention further contemplates a pharmaceutical composition comprising the polypeptide sequence of TPD IFN-α 2b, wherein the protein is O-glycosylated at Thr-106 with N-Acetyl-Galactosamine, Galactose, N-Acetyl-Glucosamine, Sialic acid, and combinations thereof.

Another aspect of the invention provides an isolated polynucleotide sequence comprising the optimized coding sequence of human erythropoietin (EPO), i.e., recombinant transgenic poultry derived erythropoietin coding sequence which codes for transgenic poultry derived erythropoietin (TPD EPO).

Yet another aspect of the invention provides for a vector comprising a first and second coding sequence and a promoter in operational and positional relationship to the first and second coding sequence to express the first and second coding sequence in an avian oviduct. The vector further includes an internal ribosome entry site (IRES) element positioned between the first and second coding sequence, wherein the first coding sequence codes for protein X and the second coding sequence codes for protein Y, and wherein protein X and protein Y are deposited into the egg white of a hard shell egg. For example, protein X may be a light chain (LC) of a monoclonal antibody and protein Y may be a heavy chain (HC) of a monoclonal antibody. Alternatively, the protein encoded by the second coding sequence (e.g., enzyme) may be capable of providing post-translational modification of the protein encoded by the first coding sequence. The vector optionally includes additional coding sequences and additional IRES elements, such that each coding sequence in the vector is separated from another coding sequence by an IRES element.

The invention also contemplates methods of producing an avian egg which contains proteins such as monoclonal antibodies, enzymes, or other proteins. Such a method includes providing a vector with a promoter, coding sequences, and at least one IRES element; creating transgenic cells or tissue by introducing the vector into avian embryonic blastodermal cells, wherein the vector sequence is randomly inserted into the avian genome; and deriving a mature transgenic avian from the transgenic cells or tissue. The transgenic avian so derived expresses the coding sequences in its oviduct, and the resulting protein is secreted into the oviduct lumen, so that the protein is deposited into the egg white of a hard shell egg.

BRIEF DESCRIPTION OF THE DRAWINGS

FIGS. 2A, 2B, 2C and 2D illustrate retroviral vectors of the invention comprising an ovalbumin promoter and a coding sequence, gene X, encoding an exogenous protein X. X represents any exogenous gene or exogenous protein of interest.

FIG. 2E illustrates a method of amplifying an exogenous gene for insertion into the vectors of 2A and 2B.

In FIG. 4A the concentration of bioactive lactamase in the serum of G0 chickens transduced with the NLB-CMV-BL transgene was measured at 8 month posthatch. The generation, sex and wing band numbers are indicated. Lactamase serum concentrations were measured for G1 transgenic chickens at 6 to 7 months post-hatch. Arrows indicate G1 chickens bred from rooster 2395. In FIG. 4B the lactamase serum concentration was measured for G1 and G2 transgenic chickens. Arrows indicate G2s bred from hen 5657 or rooster 4133. Samples from chickens 4133, 5308, and 5657 are the same as those in FIG. 4A. Samples from G2 birds bred from 5657 were collected at 3 to 60 days post-hatch. Samples from G2 birds bred from 4133 were collected at 3 month post-hatch.

FIG. 5 shows the pedigree of chickens bearing the transgenic loci harbored by hen 5657 (FIG. 5A) or rooster 4133 (FIG. 5B). 2395 was a rooster that carried multiple transgenic loci. 2395 was bred to a non-transgenic hen, yielding 3 offspring each carrying the transgene in a unique position of the chicken genome. For simplicity, transgenic progeny for which expression data were not shown as well as non-transgenic progeny were omitted from the pedigree. Band numbers are indicated by the following symbols: ○ hen; □ rooster; ● hen carrying the NLB-CMV-BL transgene; ■ rooster carrying the NLB-CMV-BL transgene.

In FIG. 6A egg white from hen 5657 and her transgenic offspring were assayed for active lactamase. The control is from untreated hens and clutchmate is a non-transgenic G2 bred from hen 5657. Eggs were collected in March 2000. Arrows indicate G2s bred from hen 5657. In FIG. 6B egg white samples from G2 transgenic hens carrying one copy of the transgene (hemizygous) were compared with that of G3 hen 6978 which harbored two copies (homozygous). Eggs were collected in February 2001. The generation and wing band numbers are indicated to the left.

In FIG. 7A egg whites from four representative hemizygous transgenic hens bred from rooster 4133 were assayed for active lactamase. Eggs were collected in October 1999, March, 2000 and February 2001 and a minimum of 4 eggs per hen were assayed one month after each set was collected. The control represents egg white from untreated hens. Band numbers are indicated to the left. The average of the 4 hens for each period is calculated. In FIG. 7B egg white from hemizygous G2 transgenic hens were compared with that of hemizygous and homozygous transgenic G3 hens. The eggs were collected in February 2001. The generation and transgene copy number are displayed in the data bar for each hen. The average concentration for hens carrying one or two copies is at the bottom of the chart.

FIG. 11 depicts the synthetic amino acid sequence (residues 1-165) of transgenic poultry derived interferon-α 2b (TPD IFN-α 2b) (SEQ ID NO: 2).

FIG. 12A depicts the synthetic nucleic acid sequence (cDNA, residues 1-579) of optimized human erythropoietin (EPO) i.e., recombinant TPD EPO (SEQ ID NO: 3).

FIG. 12B depicts the synthetic amino acid sequence (residues 1-193) of transgenic poultry derived erythropoietin (TPD EPO) (SEQ ID NO: 4). (For natural human EPO see also NCBI Accession Number NP_000790).

FIG. 13 shows the synthetic MDOT promoter linked to the IFN-MM CDS. The MDOT promoter contains elements from the chicken ovomucoid gene (ovomucoid promoter) ranging from −435 to −166 bp (see NCBI Accession Number J00894) and the chicken conalbumin gene (ovotransferrin promoter) ranging from −251 to +29 bp (see NCBI Accession Numbers Y00497, M11862 and X01205).

FIG. 14 provides a summary of the major egg white proteins.

FIGS. 15A and 15D show the pCMV-LC-emcvIRES-HC vector, wherein the light chain (LC) and heavy chain (HC) of a human monoclonal antibody were expressed from this single vector by placement of an IRES from the encephalomyocarditis virus (EMCV) in order to test for expression of monoclonal antibodies. In comparison, FIGS. 15B and 15C show the separate vectors pCMV-HC and pCMV-LC, respectively, wherein these vectors were also used to test for expression of monoclonal antibodies.

Figure 1:
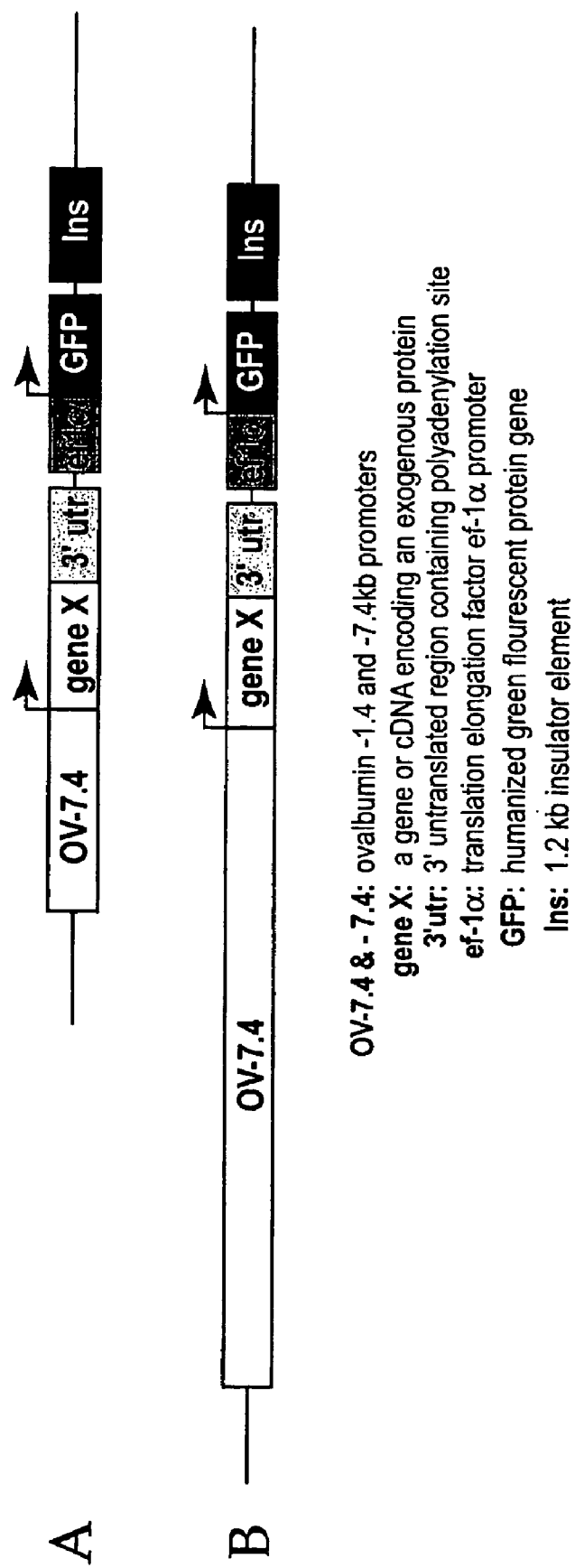
FIGS. 1A and 1B illustrate ovalbumin promoter expression vectors comprising ovalbumin promoter segments and a coding sequence, gene X, which encodes an exogenous protein X. X represents any exogenous gene or exogenous protein of interest.

DETAILED DESCRIPTION OF THE INVENTION a) Definition and General Parameters

The following definitions are set forth to illustrate and define the meaning and scope of the various terms used to describe the invention herein.

A "nucleic acid or polynucleotide sequence" includes, but is not limited to, eukaryotic mRNA, cDNA, genomic DNA, and synthetic DNA and RNA sequences, comprising the natural nucleoside bases adenine, guanine, cytosine, thymidine, and uracil. The term also encompasses sequences having one or more modified bases.

A "coding sequence" or "open reading frame" refers to a polynucleotide or nucleic acid sequence which can be transcribed and translated (in the case of DNA) or translated (in the case of mRNA) into a polypeptide in vitro or in vivo when placed under the control of appropriate regulatory sequences. The boundaries of the coding sequence are determined by a translation start codon at the 5' (amino) terminus and a translation stop codon at the 3' (carboxy) terminus. A transcription termination sequence will usually be located 3' to the coding sequence. A coding sequence may be flanked on the 5' and/or 3' ends by untranslated regions.

"Exon" refers to that part of a gene which, when transcribed into a nuclear transcript, is "expressed" in the cytoplasmic mRNA after removal of the introns or intervening sequences by nuclear splicing.

Nucleic acid "control sequences" or "regulatory sequences" refer to promoter sequences, translational start and stop codons, ribosome binding sites, polyadenylation signals, transcription termination sequences, upstream regulatory domains, enhancers, and the like, as necessary and sufficient for the transcription and translation of a given coding sequence in a defined host cell. Examples, of control sequences suitable for eukaryotic cells are promoters, polyadenylation signals, and enhancers. All of these control sequences need not be present in a recombinant vector so long as those necessary and sufficient for the transcription and translation of the desired gene are present.

"Operably or operatively linked" refers to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "heterologous" and "exogenous" as they relate to nucleic acid sequences such as coding sequences and control sequences, denote sequences that are not normally associated with a region of a recombinant construct or with a particular chromosomal locus, and/or are not normally associated with a particular cell. Thus, an "exogenous" region of a nucleic acid construct is an identifiable segment of nucleic acid within or attached to another nucleic acid molecule that is not found in association with the other molecule in nature. For example, an exogenous region of a construct could include a coding sequence flanked by sequences not found in association with the coding sequence in nature. Another example of an exogenous coding sequence is a construct where the coding sequence itself is not found in nature (e.g., synthetic sequences having codons different from the native gene). Similarly, a host cell transformed with a construct which is not normally present in the host cell would be considered exogenous for purposes of this invention.

"Exogenous protein" as used herein refers to a protein not naturally present in a particular tissue or cell, a protein that is the expression product of an exogenous expression construct or transgene, or a protein not naturally present in a given quantity in a particular tissue or cell.

"Endogenous gene" refers to a naturally occurring gene or fragment thereof normally associated with a particular cell.

The expression products described herein may consist of proteinaceous material having a defined chemical structure. However, the precise structure depends on a number of factors, particularly chemical modifications common to proteins. For example, since all proteins contain ionizable amino and carboxyl groups, the protein may be obtained in acidic or basic salt form, or in neutral form. The primary amino acid sequence may be derivatized using sugar molecules (glycosylation) or by other chemical derivatizations involving covalent or ionic attachment with, for example, lipids, phosphate, acetyl groups and the like, often occurring through association with saccharides. These modifications may occur in vitro, or in vivo, the latter being performed by a host cell through posttranslational processing systems. Such modifications may increase or decrease the biological activity of the molecule, and such chemically modified molecules are also intended to come within the scope of the invention.

Alternative methods of cloning, amplification, expression, and purification will be apparent to the skilled artisan. Representative methods are disclosed in Sambrook, Fritsch, and Maniatis, *Molecular Cloning, a Laboratory Manual*, 2nd Ed., Cold Spring Harbor Laboratory (1989).

"Vector" means a polynucleotide comprised of single strand, double strand, circular, or supercoiled DNA or RNA. A typical vector may be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements may be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An intron optionally may be included in the construct, preferably ≧100 bp 5' to the coding sequence. A vector is constructed so that the particular coding sequence is located in the vector with the appropriate regulatory sequences, the positioning and orientation of the coding sequence with respect to the control sequences being such that the coding sequence is transcribed under the "control" of the control or regulatory sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

A "promoter" is a site on the DNA to which RNA polymerase binds to initiate transcription of a gene. In some embodiments the promoter will be modified by the addition or deletion of sequences, or replaced with alternative sequences, including natural and synthetic sequences as well as sequences which may be a combination of synthetic and natural sequences. Many eukaryotic promoters contain two types of recognition sequences: the TATA box and the upstream promoter elements. The former, located upstream of the transcription initiation site, is involved in directing RNA polymerase to initiate transcription at the correct site, while the latter appears to determine the rate of transcription and is upstream of the TATA box. Enhancer elements can also stimulate transcription from linked promoters, but many function exclusively in a particular cell type. Many enhancer/promoter elements derived from viruses, e.g., the SV40 promoter, the cytomegalovirus (CMV) promoter, the rous-sarcoma virus (RSV) promoter, and the murine leukemia virus (MLV) promoter are all active in a wide array of cell types, and are termed "constitutive" or "ubiquitous". Alternatively, non-constitutive promoters such as the mouse mammary tumor virus (MMTV) promoter may also be used in the instant invention. The nucleic acid sequence inserted in the cloning site may have any open reading frame encoding a polypeptide of interest, with the proviso that where the coding sequence encodes a polypeptide of interest, it should lack cryptic splice sites which can block production of appropriate mRNA molecules and/or produce aberrantly spliced or abnormal mRNA molecules.

A "marker gene" is a gene which encodes a protein that allows for identification and isolation of correctly transfected cells. Suitable marker sequences include, but are not limited to green, yellow, and blue fluorescent protein genes (GFP, YFP, and BFP, respectively). Other suitable markers include thymidine kinase (tk), dihydrofolate reductase (DHFR), and aminoglycoside phosphotransferase (APH) genes. The latter imparts resistance to the aminoglycoside antibiotics, such as kanamycin, neomycin, and geneticin. These, and other marker genes such as those encoding chloramphenicol acetyltransferase (CAT), β-lactamase, β-galactosidase (β-gal), may be incorporated into the primary nucleic acid cassette along with the gene expressing the desired protein, or the selection markers may be contained on separate vectors and cotransfected.

A "reporter gene" is a marker gene that "reports" its activity in a cell by the presence of the protein that it encodes.

A "retroviral particle", "transducing particle", or "transduction particle" refers to a replication-defective or replication-competent virus capable of transducing non-viral DNA or RNA into a cell.

The terms "transformation", "transduction" and "transfection" all denote the introduction of a polynucleotide into an avian blastodermal cell.

"Magnum" is that part of the oviduct between the infundibulum and the isthmus containing tubular gland cells that synthesize and secrete the egg white proteins of the egg.

A "MDOT promoter", as used herein, is a synthetic promoter which is active in the tubular gland cells of the magnum of the oviduct amongst other tissues. MDOT is comprised of elements from the ovomucoid (MD) and ovotransferrin (OT) promoters (FIG. 13).

The term "optimized" is used in the context of "optimized coding sequence", wherein the most frequently used codons for each particular amino acid found in the egg white proteins ovalbumin, lysozyme, ovomucoid, and ovotransferrin are used in the design of the optimized human interferon-α 2b (IFN-α 2b) polynucleotide sequence that is inserted into vectors of the instant invention. More specifically, the DNA sequence for optimized human IFN-α 2b is based on the hen oviduct optimized codon usage and is created using the BACKTRANSLATE program of the Wisconsin Package, Version 9.1 (Genetics Computer Group Inc., Madison, Wis.) with a codon usage table compiled from the chicken (Gallus gallus) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU is used as the codon for the majority of alanines in the optimized human IFN-α 2b coding sequence. The vectors containing the gene for optimized human IFN-α 2b are used to create transgenic avians that express transgenic poultry derived IFN-α 2b (TPD IFN-α 2b) in their tissues and eggs. Similarly, the above method is employed for the design of the optimized human erythropoietin (EPO) polynucleotide sequence in order to create transgenic avians that express transgenic poultry derived erythropoietin (TPD EPO) in their tissues and eggs.

b) Novel Vectors and Transgenesis of Blastorermal Cells

By the methods of the present invention, transgenes can be introduced into avian embryonic blastodermal cells, to produce a transgenic chicken or transgenic turkey, or other avian species, that carries the transgene in the genetic material of its germ-line tissue. The blastodermal cells are typically stage VII-XII cells, or the equivalent thereof, and preferably are near stage X. The cells useful in the present invention include embryonic germ (EG) cells, embryonic stem (ES) cells & primordial germ cells (PGCs). The embryonic blastodermal cells may be isolated freshly, maintained in culture, or reside within an embryo.

The vectors useful in carrying out the methods of the present invention are described herein. These vectors may be used for stable introduction of an exogenous coding sequence into the genome of an avian. Alternatively, the vectors may be used to produce exogenous proteins in specific tissues of an avian, and in the oviduct in particular. The vectors may also be used in methods to produce avian eggs which contain exogenous protein. In a preferred embodiment, the vector is retroviral and the coding sequence and the promoter are both positioned between the 5' and 3' LTRs of the retroviral vector. In another preferred embodiment, the retroviral vector is derived from the avian leukosis virus (ALV), murine leukemia virus (MLV), or lentivirus. In another preferred embodiment, the vector includes a signal peptide coding sequence which is operably linked to the coding sequence, so that upon translation in a cell, the signal peptide will direct secretion of the exogenous protein expressed by the vector into the egg white of a hard shell egg. In yet another preferred embodiment, the vector further includes a marker gene, wherein said marker gene is operably linked to the promoter.

In some cases, introduction of a vector of the present invention into the embryonic blastodermal cells is performed with embryonic blastodermal cells that are either freshly isolated or in culture. The transgenic cells are then typically injected into the subgerminal cavity beneath a recipient blastoderm in an egg. In some cases, however, the vector is delivered directly to the cells of a blastodermal embryo.

In one embodiment of the invention, vectors used for transfecting blastodermal cells and generating random, stable integration into the avian genome contain a coding sequence and a promoter in operational and positional relationship to express the coding sequence in the tubular gland cell of the magnum of the avian oviduct, wherein the coding sequence codes for an exogenous protein which is deposited in the egg white of a hard shell egg. The promoter may optionally be a segment of the ovalbumin promoter region which is sufficiently large to direct expression of the coding sequence in the tubular gland cells. The invention involves truncating the ovalbumin promoter and/or condensing the critical regulatory elements of the ovalbumin promoter so that it retains sequences required for expression in the tubular gland cells of the magnum of the oviduct, while being small enough that it can be readily incorporated into vectors. In a preferred embodiment, a segment of the ovalbumin promoter region may be used. This segment comprises the 5'-flanking region of the ovalbumin gene. The total length of the ovalbumin promoter segment may be from about 0.88 kb to about 7.4 kb in length, and is preferably from about 0.88 kb to about 1.4 kb in length. The segment preferably includes both the steroid-dependent regulatory element and the negative regulatory element of the ovalbumin gene. The segment optionally also includes residues from the 5' untranslated region (5' UTR) of the ovalbumin gene. Hence, the promoter may be derived from the promoter regions of the ovalbumin-, lysozyme-, conalbumin-, ovomucoid-, ovotransferrin- or ovomucin genes (FIG. 14). An example of such a promoter is the synthetic MDOT promoter which is comprised of elements from the ovomucoid and ovotransferrin promoter (FIG. 13). The promoter may also be a promoter that is largely, but not entirely, specific to the magnum, such as the lysozyme promoter. The promoter may also be a mouse mammary tumor virus (MMTV) promoter. Alternatively, the promoter may be a constitutive promoter (e.g., a cytomegalovirus (CMV) promoter, a rous-sarcoma virus (RSV) promoter, a murine leukemia virus (MLV) promoter, etc.). In a preferred embodiment of the invention, the promoter is a cytomegalovirus (CMV) promoter, a MDOT promoter, a rous-sarcoma virus (RSV) promoter, a murine leukemia virus (MLV) promoter, a mouse mammary tumor virus (MMTV) promoter, an ovalbumin promoter, a lysozyme promoter, a conalbumin promoter, an ovomucoid promoter, an ovomucin promoter, and an ovotransferrin promoter. Optionally, the promoter may be at least one segment of a promoter region, such as a segment of the ovalbumin-, lysozyme-, conalbumin-, ovomucoid-, ovomucin-, and ovotransferrin promoter region. In a particularly preferred embodiment, the promoter is a CMV promoter.

FIGS. 1A and 1B illustrate examples of ovalbumin promoter expression vectors. Gene X is a coding sequence which encodes an exogenous protein. Bent arrows indicate the transcriptional start sites. In one example, the vector contains 1.4 kb of the 5' flanking region of the ovalbumin gene (FIG. 1A). The sequence of the "−1.4 kb promoter" of FIG. 1A corresponds to the sequence starting from approximately 1.4 kb upstream (1.4 kb) of the ovalbumin transcription start site and extending approximately 9 residues into the 5' untranslated region of the ovalbumin gene. The approximately 1.4 kb-long segment harbors two critical regulatory elements, the steroid-dependent regulatory element (SDRE) and the negative regulatory element (NRE). The NRE is so named because it contains several negative regulatory elements which block the gene's expression in the absence of hormones (e.g., estrogen). A shorter 0.88 kb segment also contains both elements. In another example, the vector contains approximately 7.4 kb of the 5' flanking region of the ovalbumin gene and harbors two additional elements (HS-III and HS-IV), one of which is known to contain a functional region enabling induction of the gene by estrogen (FIG. 1B). A shorter 6 kb segment also contains all four elements and could optionally be used in the present invention.

Each vector used for random integration according to the present invention preferably comprises at least one 1.2 kb element from the chicken β-globin locus which insulates the gene within from both activation and inactivation at the site of insertion into the genome. In a preferred embodiment, two insulator elements are added to one end of the ovalbumin gene construct. In the β-globin locus, the insulator elements serve to prevent the distal locus control region (LCR) from activating genes upstream from the globin gene domain, and have been shown to overcome position effects in transgenic flies, indicating that they can protect against both positive and negative effects at the insertion site. The insulator element(s) are only needed at either the 5' or 3' end of the gene because the transgenes are integrated in multiple, tandem copies effectively creating a series of genes flanked by the insulator of the neighboring transgene. In another embodiment, the insulator element is not linked to the vector but is cotransfected with the vector. In this case, the vector and the element are joined in tandem in the cell by the process of random integration into the genome.

Each vector may optionally also comprise a marker gene to allow identification and enrichment of cell clones which have stably integrated the expression vector. The expression of the marker gene is driven by a ubiquitous promoter that drives high levels of expression in a variety of cell types. In a preferred embodiment of the invention, the marker gene is human interferon driven by a lysozyme promoter. In another embodiment the green fluorescent protein (GFP) reporter gene (Zolotukhin et al., J. Virol 70:4646-4654 (1995)) is driven by the Xenopus elongation factor 1-α (ef-1 α) promoter (Johnson and Krieg, Gene 147:223-26 (1994)). The Xenopus ef-1 α promoter is a strong promoter expressed in a variety of cell types. The GFP contains mutations that enhance its fluorescence and is humanized, or modified such that the codons match the codon usage profile of human genes. Since avian codon usage is virtually the same as human codon usage, the humanized form of the gene is also highly expressed in avian blastodermal cells. In alternative embodiments, the marker gene is operably linked to one of the ubiquitous promoters of HSV tk, CMV, β-actin, or RSV.

While human and avian codon usage is well matched, where a nonvertebrate gene is used as the coding sequence in the transgene, the nonvertebrate gene sequence may be modified to change the appropriate codons such that codon usage is similar to that of humans and avians.

Transfection of the blastodermal cells may be mediated by any number of methods known to those of ordinary skill in the art. The introduction of the vector to the cell may be aided by first mixing the nucleic acid with polylysine or cationic lipids which help facilitate passage across the cell membrane. However, introduction of the vector into a cell is preferably achieved through the use of a delivery vehicle such as a liposome or a virus. Viruses which may be used to introduce the vectors of the present invention into a blastodermal cell include, but are not limited to, retroviruses, adenoviruses, adeno-associated viruses, herpes simplex viruses, and vaccinia viruses.

In one method of transfecting blastodermal cells, a packaged retroviral-based vector is used to deliver the vector into embryonic blastodermal cells so that the vector is integrated into the avian genome.

As an alternative to delivering retroviral transduction particles to the embryonic blastodermal cells in an embryo, helper cells which produce the retrovirus can be delivered to the blastoderm.

A preferred retrovirus for randomly introducing a transgene into the avian genome is the replication-deficient avian leucosis virus (ALV), the replication-deficient murine leukemia virus (MLV), or the lentivirus. In order to produce an appropriate retroviral vector, a pNLB vector is modified by inserting a region of the ovalbumin promoter and one or more exogenous genes between the 5' and 3' long terminal repeats (LTRs) of the retrovirus genome. Any coding sequence placed downstream of the ovalbumin promoter will be expressed in the tubular gland cells of the oviduct magnum because the ovalbumin promoter drives the expression of the ovalbumin protein and is active in the oviduct tubular gland cells. While a 7.4 kb ovalbumin promoter has been found to produce the most active construct when assayed in cultured oviduct tubular gland cells, the ovalbumin promoter is preferably shortened for use in the retroviral vector. In a preferred embodiment, the retroviral vector comprises a 1.4 kb segment of the ovalbumin promoter; a 0.88 kb segment would also suffice.

Any of the vectors of the present invention may also optionally include a coding sequence encoding a signal peptide that will direct secretion of the protein expressed by the vector's coding sequence from the tubular gland cells of the oviduct. This aspect of the invention effectively broadens the spectrum of exogenous proteins that may be deposited in avian eggs using the methods of the invention. Where an exogenous protein would not otherwise be secreted, the vector bearing the coding sequence is modified to comprise a DNA sequence comprising about 60 bp encoding a signal peptide from the lysozyme gene. The DNA sequence encoding the signal peptide is inserted in the vector such that it is located at the N-terminus of the protein encoded by the cDNA.

FIGS. 2A-2D illustrate examples of suitable retroviral vector constructs. The vector construct is inserted into the avian genome with 5' and 3' flanking LTRs. Neo is the neomycin phosphotransferase gene. Bent arrows indicate transcription start sites. FIGS. 2A and 2B illustrate LTR and oviduct transcripts with a sequence encoding the lysozyme signal peptide (LSP), whereas FIGS. 2C and 2D illustrate transcripts without such a sequence. There are two parts to the retroviral vector strategy. Any protein that contains a eukaryotic signal peptide may be cloned into the vectors depicted in FIGS. 2B and 2D. Any protein that is not ordinarily secreted may be cloned into the vectors illustrated in FIGS. 2A and 2B to enable its secretion from the tubular gland cells.

FIG. 2E illustrates the strategy for cloning an exogenous gene into a lysozyme signal peptide vector. The polymerase chain reaction is used to amplify a copy of a coding sequence, gene X, using a pair of oligonucleotide primers containing restriction enzyme sites that enable the insertion of the amplified gene into the plasmid after digestion with the two enzymes. The 5' and 3' oligonucleotides contain the Bsu36I and Xba1 restriction sites, respectively.

Figure 2F:
FIG. 2F illustrates a retroviral vector comprising an ovalbumin promoter controlling expression of a coding sequence, gene X, and an internal ribosome entry site (IRES) element enabling expression of a second coding sequence, gene Y. X and Y represent any gene of interest.

Another aspect of the invention involves the use of internal ribosome entry site (IRES) elements in any of the vectors of the present invention to allow the translation of two or more proteins from a di- or polycistronic mRNA (Example 15). The IRES units are fused to 5' ends of one or more additional coding sequences which are then inserted into the vectors at the end of the original coding sequence, so that the coding sequences are separated from one another by an IRES (FIGS. 2F, 15A and 15D). Pursuant to this aspect of the invention, post-translational modification of the product is facilitated because one coding sequence may encode an enzyme capable of modifying the other coding sequence product. For example, the first coding sequence may encode collagen which would be hydroxylated and made active by the enzyme encoded by the second coding sequence. In the retroviral vector example of FIG. 2F, an internal ribosome entry site (IRES) element is positioned between two exogenous coding sequences (gene X and gene Y). The IRES allows both protein X and protein Y to be translated from the same transcript directed by an ovalbumin promoter. Bent arrows indicate transcription start sites. The expression of the protein encoded by gene X is expected to be highest in tubular gland cells, where it is specifically expressed but not secreted. The protein encoded by gene Y is also expressed specifically in tubular gland cells but because it is efficiently secreted, protein Y is packaged into the eggs. In the retroviral vector example of FIGS. 15A and 15D, the light chain (LC) and heavy chain (HC) of a human monoclonal antibody are expressed from a single vector, pCMV-LC-emcvIRES-HC, by placement of an IRES from the encephalomyocarditis virus (EMCV). Transcription is driven by a CMV promoter. (See also Murakami et al. (1997) "High-level expression of exogenous genes by replication-competent retrovirus vectors with an internal ribosomal entry site" *Gene* 202:23-29; Chen et al. (1999) "Production and design of more effective avian replication-incompetent retroviral vectors" *Dev. Biol.* 214:370-384; Noel et al. (2000) "Sustained systemic delivery of monoclonal antibodies by genetically modified skin fibroblasts" *J. Invest. Dermatol.* 115:740-745.)

In another aspect of the invention, the coding sequences of vectors used in any of the methods of the present invention are provided with a 3' untranslated region (3' UTR) to confer stability to the RNA produced. When a 3' UTR is added to a retroviral vector, the orientation of the fused ovalbumin promoter, gene X and the 3' UTR must be reversed in the construct, so that the addition of the 3' UTR will not interfere with transcription of the full-length genomic RNA. In a preferred embodiment, the 3' UTR may be that of the ovalbumin or lysozyme genes, or any 3' UTR that is functional in a magnum cell, i.e., the SV40 late region.

In an alternative embodiment of the invention, a constitutive promoter (e.g., CMV) is used to express the coding sequence of a transgene in the magnum of an avian. In this case, expression is not limited to the magnum; expression also occurs in other tissues within the avian (e.g., blood). The use of such a transgene, which includes a constitutive promoter and a coding sequence, is particularly suitable for effecting the expression of a protein in the oviduct and the subsequent secretion of the protein into the egg white (see FIG. 8A for an example of a CMV driven construct, such as the pNLB-CMV-IFN vector for expressing IFN-α 2b in chickens).

Figure 3:
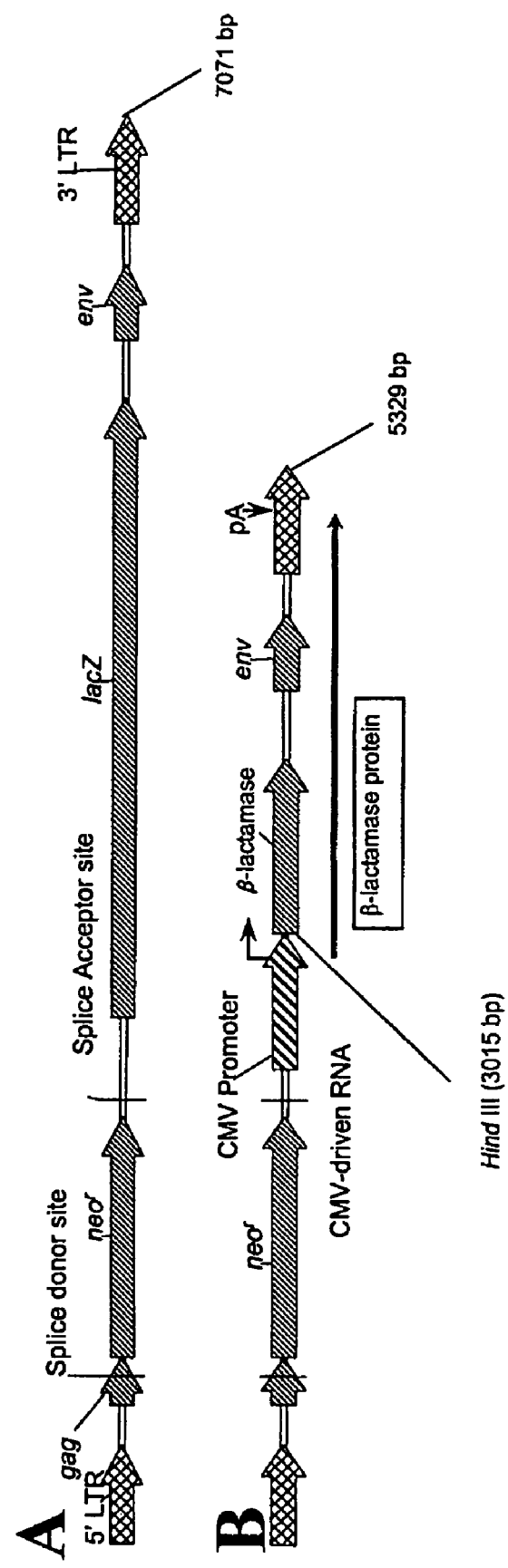
FIGS. 3A and 3B show schematic representations of the ALV-derived vectors pNLB and pNLB-CMV-BL, respectively. Because NLB has not been sequenced in its entirety, measurements in bp (base pair) are estimated from published data (Cosset et al., 1991; Thoraval et al., 1995) and data discussed herein. The vectors are both shown as they would appear while integrated into the chicken genome.

FIG. 3A shows a schematic of the replication-deficient avian leukosis virus (ALV)-based vector pNLB, a vector which is suitable for use in this embodiment of the invention. In the pNLB vector, most of the ALV genome is replaced by the neomycin resistance gene (Neo) and the lacZ gene, which encodes b-galactosidase. FIG. 3B shows the vector pNLB-CMV-BL, in which lacZ has been replaced by the CMV promoter and the β-lactamase coding sequence (β-La or BL). Construction of the vector is reported in the specific examples (Example 1, vide infra). β-lactamase is expressed from the CMV promoter and utilizes a polyadenylation signal (pA) in the 3' long terminal repeat (LTR). The β-Lactamase protein has a natural signal peptide; thus, it is found in blood and in egg white.

Avian embryos are transduced with the pNLB-CMV-BL vector (Example 2, vide infra). The egg whites of eggs from the resulting stably transduced hens contain up to 60 micrograms (μg) of secreted, active β-lactamase per egg (Examples 2 and 3, vide infra).

Figure 8:
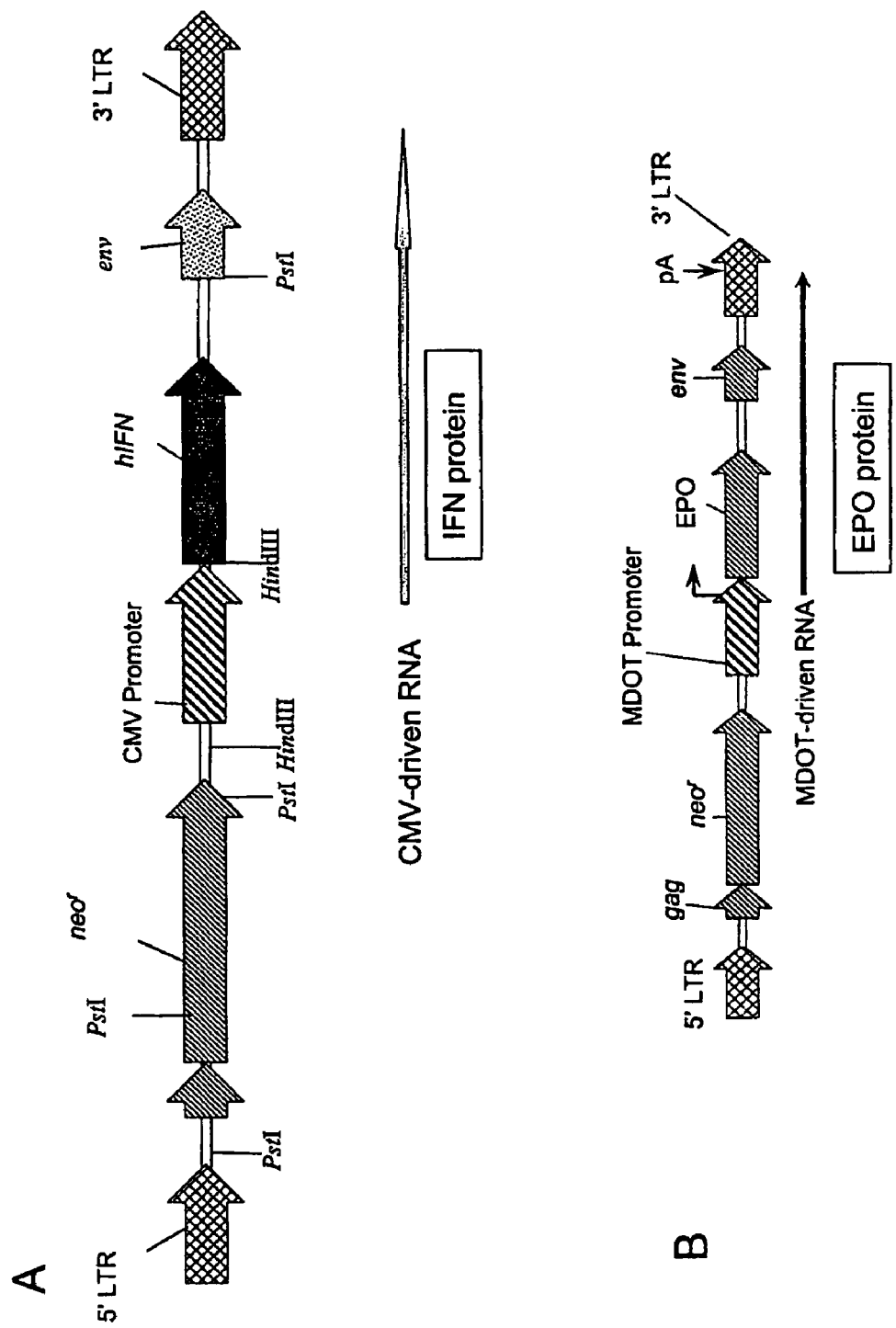
FIGS. 8A and 8B show the pNLB-CMV-IFN vector for expressing IFN-α 2b in chickens; and the pNLB-MDOT-EPO vector used for expressing erythropoietin (EPO) in chickens, respectively.

FIGS. 8A and 8B illustrates the pNLB-CMV-IFN vector used for expressing interferon-α 2b (IFN-α 2b) and the pNLB-MDOT-EPO vector used for expressing erythropoietin (EPO), respectively. Both exogenous proteins (EPO, IFN) are expressed in avians, preferably chicken and turkey.

The pNLB-MDOT-EPO vector is created by substituting an EPO encoding sequence for the BL encoding sequence (Example 10, vide infra). In one embodiment, a synthetic promoter called MDOT is employed to drive expression of EPO. MDOT contains elements from both the ovomucoid and ovotransferrin promoter. The DNA sequence for human EPO is based on hen oviduct optimized codon usage as created using the BACKTRANSLATE program of the Wisconsin Package, version 9.1 (Genetics Computer Group, Inc., Madison, Wis.) with a codon usage table compiled from the chicken (Gallus gallus) ovalbumin, lysozyme, ovomucoid, and ovotransferrin proteins. The EPO DNA sequence is synthesized and cloned into the vector and the resulting plasmid is pNLB-MDOT-EPO (a.k.a. pAVIJCR-A145.27.2.2). In one embodiment, transducing particles (i.e., transduction particles) are produced for the vector, and these transducing particles are titered to determine the appropriate concentration that can be used to inject embryos. Eggs are then injected with transducing particles after which they hatch about 21 days later. The exogenous protein levels such as the EPO levels can then be measured by an ELISA assay from serum samples collected from chicks one week after hatch. Male birds are selected for breeding, wherein birds are screened for $G_0$ roosters which contain the EPO transgene in their sperm. Preferably, roosters with the highest levels of the transgene in their sperm samples are bred to nontransgenic hens by artificial insemination. Blood DNA samples are screened for the presence of the transgene. A number of chicks are usually found to be transgenic ($G_1$ avians). Chick serum is tested for the presence of human EPO (e.g., ELISA assay). The egg white in eggs from $G_1$ hens is also tested for the presence of human EPO. The EPO (i.e., derived from the optimized coding sequence of human EPO) present in eggs of the instant invention is biologically active (Example 11).

Similarly, the pNLB-CMV-IFN vector (FIG. 8A) is created by substituting an IFN encoding sequence for the BL encoding sequence (Example 12, vide infra). In one embodiment, a constitutive cytomegalovirus (CMV) promoter is employed to drive expression of IFN. More specifically, the IFN coding sequence is controlled by the cytomegalovirus (CMV) immediate early promoter/enhancer and SV40 polyA site. FIG. 8A illustrates pNLB-CMV-IFN used for expressing IFN in avians, preferably chicken and turkey. An optimized coding sequence is created for human IFN-α 2b, wherein the most frequently used codons for each particular amino acid found in the egg white proteins ovalbumin, lysozyme, ovomucoid, and ovotransferrin are used in the design of the human IFN-α 2b sequence that is inserted into vectors of the instant invention. More specifically, the DNA sequence for the optimized human IFN-α 2b (FIG. 11A) is based on the hen oviduct optimized codon usage and is created using the BACKTRANSLATE program (supra) with a codon usage table compiled from the chicken (Gallus gallus) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU is used as the codon for the majority of alanines in the optimized human IFN-α 2b sequence. The vectors containing the gene for the optimized human IFN-α 2b sequence are used to create transgenic avians that express TPD IFN-α 2b in their tissues and eggs.

Transducing particles (i.e., transduction particles) are produced for the vector and titered to determine the appropriate concentration that can be used to inject embryos (Example 2, vide infra). Thus, chimeric avians are produced (see also Example 13, vide infra). Avian eggs are windowed according to the Speksnijder procedure (U.S. Pat. No. 5,897, 998), and eggs are injected with transducing particles. Eggs hatch about 21 days after injection. hIFN levels are measured (e.g., ELISA assay) from serum samples collected from chicks one week after hatch. As with EPO (supra), male birds are selected for breeding. In order to screen for $G_0$ roosters which contain the IFN transgene in their sperm, DNA is extracted from rooster sperm samples. The $G_0$ roosters with the highest levels of the transgene in their sperm samples are bred to nontransgenic hens by artificial insemination. Blood DNA samples are screened for the presence of the transgene. The serum of transgenic roosters is tested for the presence of hIFN (e.g., ELISA assay). If the exogenous protein is confirmed the sperm of the transgenic roosters is used for artificial insemination of nontransgenic hens. A certain percent of the offspring will then contain the transgene (e.g., more than 50%). When IFN (i.e., derived from the optimized coding sequence of human IFN) is present in eggs of the instant invention, the IFN may be tested for biological activity. As with EPO, such eggs usually contain biologically active IFN, such as TPD IFN-α 2b (FIG. 11B).

c) Production of Transgenic Avians and Exogenous Proteins in Eggs

The methods of the invention which provide for the production of exogenous protein in the avian oviduct and the production of eggs which contain exogenous protein involve an additional step subsequent to providing a suitable vector and introducing the vector into embryonic blastodermal cells so that the vector is integrated into the avian genome. The subsequent step involves deriving a mature transgenic avian from the transgenic blastodermal cells produced in the previous steps. Deriving a mature transgenic avian from the blastodermal cells optionally involves transferring the transgenic blastodermal cells to an embryo and allowing that embryo to develop fully, so that the cells become incorporated into the avian as the embryo is allowed to develop. The resulting chick is then grown to maturity. In a preferred embodiment, the cells of a blastodermal embryo are transfected or transduced with the vector directly within the embryo (Example 2). The resulting embryo is allowed to develop and the chick allowed to mature.

In either case, the transgenic avian so produced from the transgenic blastodermal cells is known as a founder. Some founders will carry the transgene in the tubular gland cells in the magnum of their oviducts. These avians will express the exogenous protein encoded by the transgene in their oviducts. The exogenous protein may also be expressed in other tissues (e.g., blood) in addition to the oviduct. If the exogenous protein contains the appropriate signal sequence(s), it will be secreted into the lumen of the oviduct and into the egg white of the egg. Some founders are germ-line founders (Examples 8 and 9). A germ-line founder is a founder that carries the transgene in genetic material of its germ-line tissue, and may also carry the transgene in oviduct magnum tubular gland cells that express the exogenous protein. Therefore, in accordance with the invention, the transgenic avian will have tubular gland cells expressing the exogenous protein, and the offspring of the transgenic avian will also have oviduct magnum tubular gland cells that express the exogenous protein. Alternatively, the offspring express a phenotype determined by expression of the exogenous gene in specific tissue(s) of the avian (Example 6, Table 2). In a preferred embodiment of the invention, the transgenic avian is a chicken or a turkey.

The invention can be used to express, in large yields and at low cost, a wide range of desired proteins including those used as human and animal pharmaceuticals, diagnostics, and livestock feed additives. Proteins such as interferon (IFN), erythropoietin (EPO), human growth hormone, lysozyme, and β-casein are examples of proteins which are desirably expressed in the oviduct and deposited in eggs according to the invention (Examples 2, 3, and 5). Other possible proteins to be produced include, but are not limited to, albumin, α-1 antitrypsin, antithrombin III, collagen, factors VIII, IX, X (and the like), fibrinogen, hyaluronic acid, insulin, lactoferrin, protein C, granulocyte colony-stimulating factor (G-CSF), granulocyte macrophage colony-stimulating factor (GM-CSF), tissue-type plasminogen activator (tPA), feed additive enzymes, somatotropin, and chymotrypsin. Genetically engineered antibodies, such as immunotoxins which bind to surface antigens on human tumor cells and destroy them, can also be expressed for use as pharmaceuticals or diagnostics.

d) Transgenic Poultry Derived Interferon-α 2b (TPD IFN-α 2b)

Figure 9:
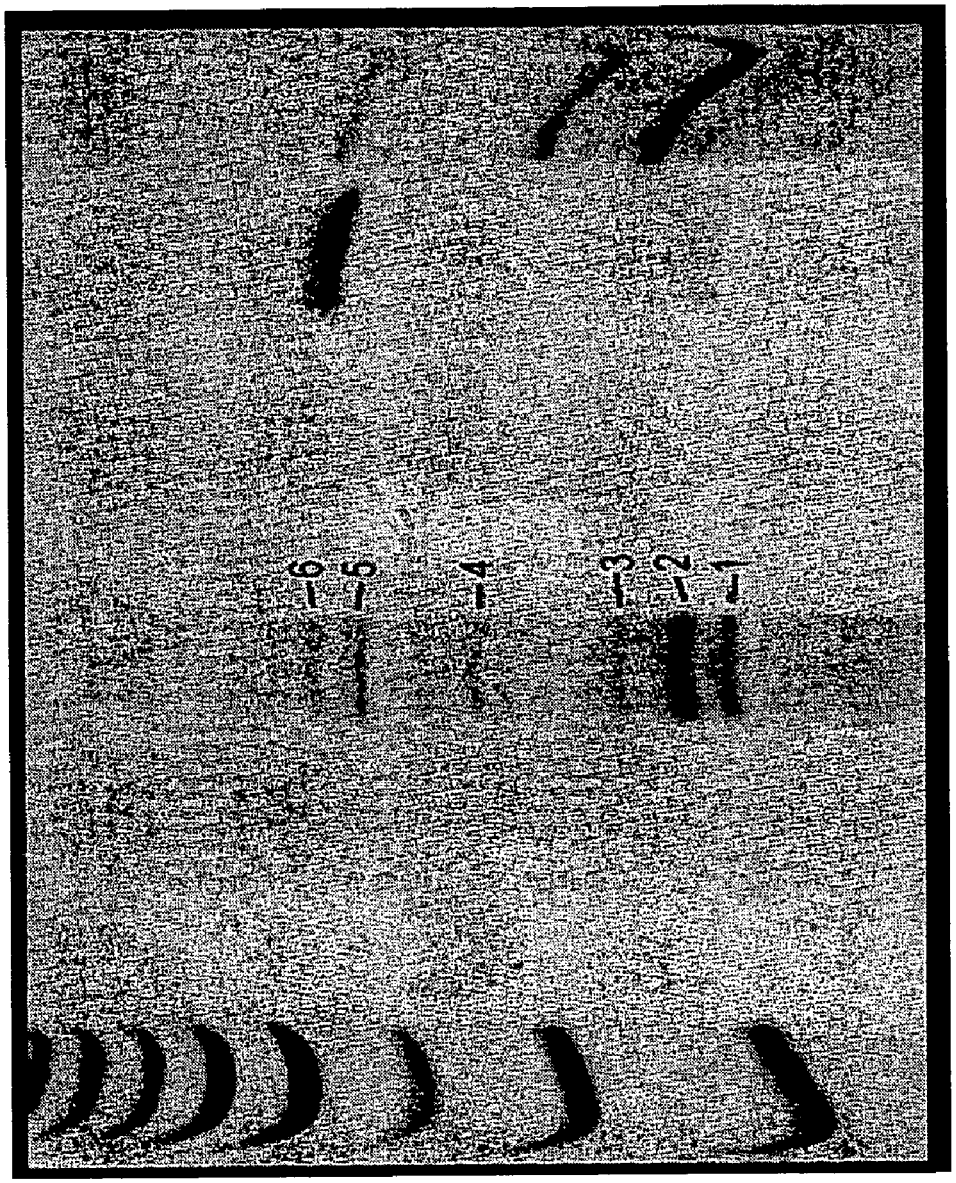
FIG. 9 depicts the novel glycosylation pattern of transgenic poultry derived interferon-α 2b (TPD IFN-α 2b), including all 6 bands.

The instant invention encompasses a transgenic poultry derived interferon-α 2b (TPD IFN-α 2b) derived from avians. TPD IFN-α 2b exhibits a new glycosylation pattern and contains two new glyco forms (bands 4 and 5 are α-Gal extended disaccharides; see FIG. 9) not normally seen in human peripheral blood leukocyte derived interferon-α 2b (PBL IFN-α 2b). TPD IFN-α 2b also contains O-linked carbohydrate structures that are similar to human PBL IFN-α 2b and is more efficiently produced in chickens then the human form.

The instant invention contemplates an isolated polynucleotide comprising the optimized polynucleotide sequence of human IFN-α 2b, i.e., recombinant transgenic poultry derived interferon-α 2b (TPD IFN-α 2b) coding sequence (SEQ ID NO: 1). The coding sequence for optimized human IFN-α 2b includes 498 nucleic acids and 165 amino acids (see SEQ ID NO: 1 and FIG. 11A). Similarly, the coding sequence for natural human IFN-α 2b includes 498 nucleic acids (NCBI Accession Number AF405539 and GI:15487989) and 165 amino acids (NCBI Accession Number AAL01040 and GI:15487990). The most frequently used codons for each particular amino acid found in the egg white proteins ovalbumin, lysozyme, ovomucoid, and ovotransferrin are used in the design of the optimized human IFN-α 2b coding sequence which is inserted into vectors of the instant invention. More specifically, the DNA sequence for the optimized human IFN-α 2b is based on the hen oviduct optimized codon usage and is created using the BACK-TRANSLATE program of the Wisconsin Package, Version 9.1 (Genetics Computer Group Inc., Madison, Wis.) with a codon usage table compiled from the chicken (Gallus gallus) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU is used as the codon for the majority of alanines in the optimized human IFN-α 2b coding sequence. The vectors containing the gene for optimized human IFN-α 2b are used to create transgenic avians that express TPD IFN-α 2b in their tissues and eggs.

Figure 10:
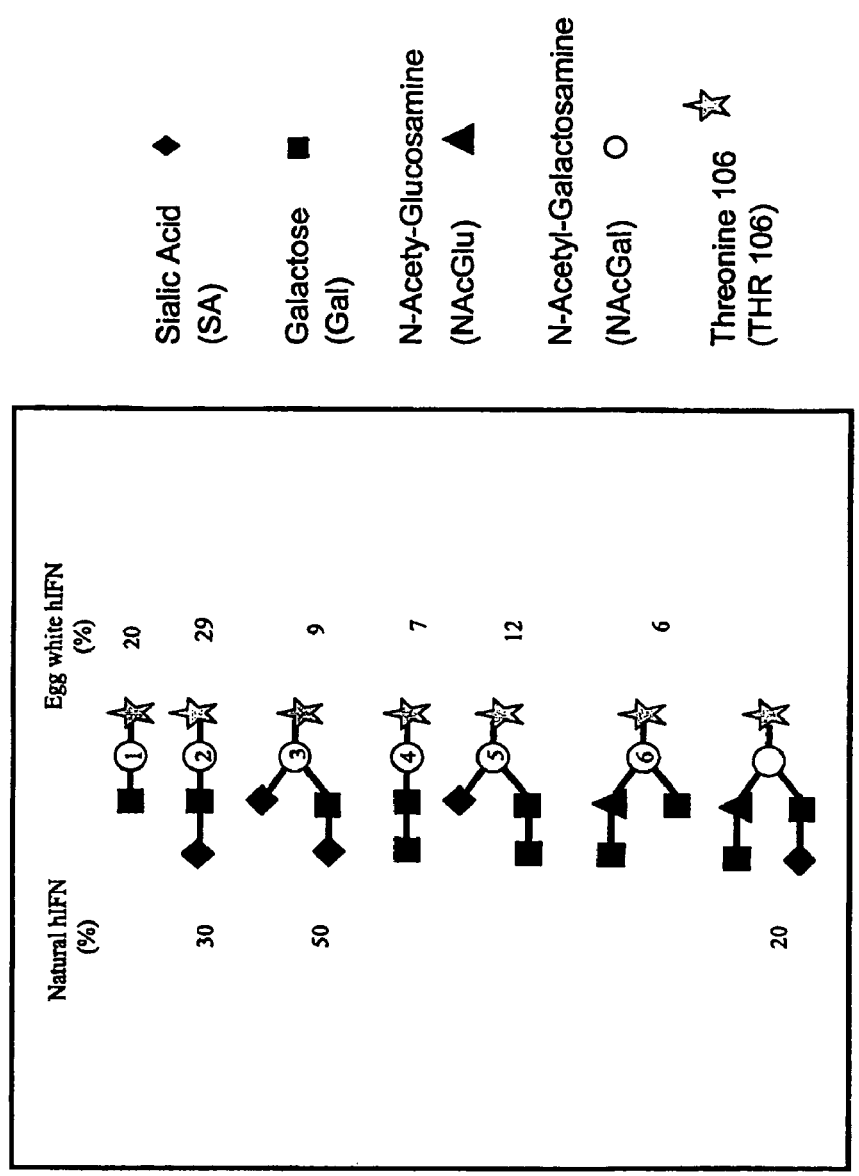
FIG. 10 shows the comparison of human peripheral blood leukocyte derived interferon-α 2b (PBL IFN-α 2b or natural hIFN) and transgenic poultry derived interferon-α 2b (TPD IFN-α 2b or egg white hIFN).

As discussed in Example 13 (vide infra), TPD IFN-α 2b is produced in chicken. However, TPD IFN-α 2b may also be produced in turkey and other avian species. In a preferred embodiment of the invention, TPD IFN-α 2b is expressed in chicken and turkey and their hard shell eggs. A carbohydrate analysis (Example 14, vide infra), including a monosaccharide analysis and FACE analysis, reveals the sugar make-up or novel glycosylation pattern of the protein. As such, TPD IFN-α 2b shows the following monosaccharide residues: N-Acetyl-Galactosamine (NAcGal), Galactose (Gal), N-Acetyl-Glucosamine (NAcGlu), and Sialic acid (SA). However, there is no N-linked glycosylation in TPD IFN-α 2b. Instead, TPD IFN-α 2b is O-glycosylated at Thr-106. This type of glycosylation is similar to human IFN-α 2, wherein the Thr residue at position 106 is unique to IFN-α 2. Similar to natural IFN-α, TPD IFN-α 2b does not have mannose residues. A FACE analysis reveals 6 bands (FIG. 9) that represent various sugar residues, wherein bands 1, 2 and 3 are un-sialyated, mono-sialyated, and di-sialyated, respectively (FIG. 10). The sialic acid (SA) linkage is alpha 2-3 to Galactose (Gal) and alpha 2-6 to N-Acetyl-Galactosamine (NAcGal). Band 6 represents an un-sialyated tetrasaccharide. Bands 4 and 5 are alpha-Galactose (alpha-Gal) extended disaccharides that are not seen in human PBL IFN-α 2b or natural human IFN (natural hIFN). FIG. 10 shows the comparison of TPD IFN-α 2b (egg white hIFN) and human PBL IFN-α 2b (natural hIFN). Minor bands are present between bands 3 and 4 and between bands 4 and 5 in TPD IFN-α 2b (vide infra).

The instant invention contemplates an isolated polypeptide sequence (SEQ ID NO: 2) of TPD IFN-α 2b (see also FIG. 11B) and a pharmaceutical composition thereof, wherein the protein is O-glycosylated at Thr-106 with specific residues. These residues are as follows:

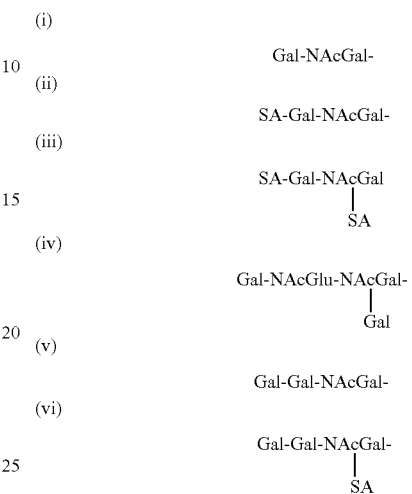

(i) Gal-NAcGal- (ii) SA-Gal-NAcGal- (iii) SA-Gal-NAcGal
          |
          SA (iv) Gal-NAcGlu-NAcGal-
            |
            Gal (v) Gal-Gal-NAcGal- (vi) Gal-Gal-NAcGal-
            |
            SA wherein Gal=Galactose,
NAcGal=N-Acetyl-Galactosamine,
NAcGlu=N-Acetyl-Glucosamine, and
SA=Sialic Acid.

In a preferred embodiment of the instant invention, the percentages are as follows:

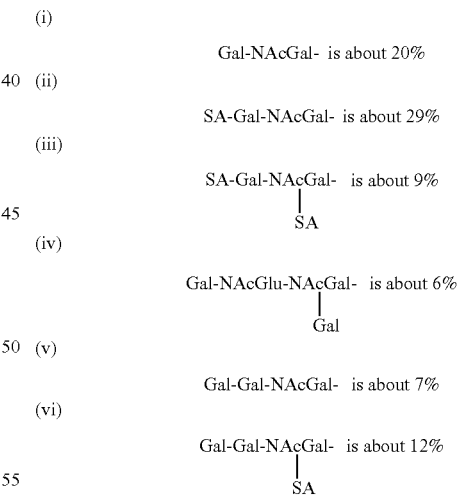

(i) Gal-NAcGal- is about 20%

(ii) SA-Gal-NAcGal- is about 29%

(iii) SA-Gal-NAcGal- is about 9%
            |
            SA (iv) Gal-NAcGlu-NAcGal- is about 6%
              |
              Gal (v) Gal-Gal-NAcGal- is about 7%

(vi) Gal-Gal-NAcGal- is about 12%
              |
              SA

Minor bands are present between bands 3 and 4 and between bands 4 and 5 which account for about 17% in TPD IFN-α 2b.

e) EXAMPLES

The following specific examples are intended to illustrate the invention and should not be construed as limiting the scope of the claims.

Example 1

Vector Construction

The lacZ gene of pNLB, a replication-deficient avian leukosis virus (ALV)-based vector (Cosset et al., 1991), was replaced with an expression cassette consisting of a cytomegalovirus (CMV) promoter and the reporter gene, β-lactamase. The pNLB and pNLB-CMV-BL vector constructs are diagrammed in FIGS. 3A and 3B, respectively.

To efficiently replace the lacZ gene of pNLB with a transgene, an intermediate adaptor plasmid was first created, pNLB-Adapter. pNLB-Adapter was created by inserting the chewed back ApaI/ApaI fragment of pNLB (Cosset et al., *J. Virol.* 65:3388-94 (1991)) (in pNLB, the 5' ApaI resides 289 bp upstream of lacZ and the 3'ApaI resides 3' of the 3' LTR and Gag segments) into the chewed-back KpnI/SacI sites of pBluescriptKS(-). The filled-in MluI/XbaI fragment of pCMV-BL (Moore et al., *Anal. Biochem.* 247: 203-9 (1997)) was inserted into the chewed-back KpnI/NdeI sites of pNLB-Adapter, replacing lacZ with the CMV promoter and the BL gene (in pNLB, KpnI resides 67 bp upstream of lacZ and NdeI resides 100 bp upstream of the lacZ stop codon), thereby creating pNLB-Adapter-CMV-BL. To create pNLB-CMV-BL, the HindIII/BlpI insert of pNLB (containing lacZ) was replaced with the HindIII/BlpI insert of pNLB-Adapter-CMV-BL. This two step cloning was necessary because direct ligation of blunt-ended fragments into the HindIII/BlpI sites of pNLB yielded mostly rearranged subclones, for unknown reasons.

Example 2

Creation of the NLB-CMV-BL Founder Flock

Sentas and Isoldes were cultured in F10 (Gibco), 5% newborn calf serum (Gibco), 1% chicken serum (Gibco), 50 μg/ml phleomycin (Cayla Laboratories) and 50 μg/ml hygromycin (Sigma). Transduction particles were produced as described in Cosset et al., 1993, herein incorporated by reference, with the following exceptions. Two days after transfection of the retroviral vector pNLB-CMV-BL (from Example 1, above) into 9×10$^5$ Sentas, virus was harvested in fresh media for 6-16 hours and filtered. All of the media was used to transduce 3×10$^6$ Isoldes in 3 100 mm plates with polybrene added to a final concentration of 4 μg/ml. The following day the media was replaced with media containing 50 μg/ml phleomycin, 50 μg/ml hygromycin and 200 μg/ml G418 (Sigma). After 10-12 days, single G418$^r$ colonies were isolated and transferred to 24-well plates. After 7-10 days, titers from each colony were determined by transduction of Sentas followed by G418 selection. Typically 2 out of 60 colonies gave titers at 1-3×10$^5$. Those colonies were expanded and virus concentrated to 2-7×10$^6$ as described in Allioli et al., *Dev. Biol.* 165:30-7 (1994), herein incorporated by reference. The integrity of the CMV-BL expression cassette was confirmed by assaying for β-lactamase in the media of cells transduced with NLB-CMV-BL transduction particles.

The transduction vector, NLB-CMV-BL, was injected into the subgerminal cavity of 546 unincubated SPF White Leghorn embryos, of which 126 chicks hatched and were assayed for secretion of β-lactamase (lactamase) into blood. In order to measure the concentration of active lactamase in unknown samples, a kinetic colorimetric assay was employed in which PADAC, a purple substrate, is converted to a yellow compound specifically by lactamase. Lactamase activity was quantitated by monitoring the decrease in $OD_{570 \, nm}$ during a standard reaction time and compared to a standard curve with varying levels of purified lactamase (referred to as the "lactamase assay"). The presence or absence of lactamase in a sample could also be determined by visually scoring for the conversion of purple to yellow in a test sample overnight or for several days (the "overnight lactamase assay"). The latter method was suitable for detection of very low levels of lactamase or for screening a large number of samples. At one to four weeks of age, chick serum samples were tested for the presence of lactamase. Twenty-seven chicks had very low levels of lactamase in their serum that was detectable only after the overnight lactamase assay and, as these birds matured, lactamase was no longer detectable. As shown in Table 1 below and FIG. 4A, 9 additional birds (3 males and 6 females) had serum levels of lactamase that ranged from 11.9 to 173.4 ng/ml at six to seven months post-hatch.

TABLE 1

Expression of β-Lactamase in NLB-CMV-BL-Transduced Chickens

| | | Average ng/ml of β-Lactamase | | |
| --- | --- | --- | --- | --- |
| Sex | Band No. | Serum: 8 Month Birds | Egg White: 8 Month Hens[3] | Egg White: 14 Month Hens[3] |
| NA[1] | Controls[2] | 0.0 ± 7.4 | 0.0 ± 13.6 | 0.0 ± 8.0 |
| Female | 1522 | 36.7 ± 1.6 | 56.3 ± 17.8 | 47.9 ± 14.3 |
| Female | 1549 | 11.9 ± 1.3 | 187.0 ± 32.4 | 157.0 ± 32.2 |
| Female | 1581 | 31.5 ± 4.8 | 243.8 ± 35.7 | 321.7 ± 68.8 |
| Female | 1587 | 33.9 ± 1.4 | 222.6 ± 27.7 | 291.0 ± 27.0 |
| Female | 1790 | 31.0 ± 0.5 | 136.6 ± 20.2 | 136.3 ± 11.0 |
| Female | 1793 | 122.8 ± 3.6 | 250.0 ± 37.0 | 232.5 ± 28.6 |
| Male | 2395 | 16.0 ± 2.3 | NA | NA |
| Male | 2421 | 165.5 ± 5.0 | NA | NA |
| Male | 2428 | 173.4 ± 5.9 | NA | NA |

[1]NA: not applicable.
[2]Controls were obtained from untreated hens.
[3]Represents the average of 5 to 20 eggs.

Example 3

β-Lactamase Expression in the Egg White of G0 Hens

Fifty-seven pullets transduced with NLB-CMV-BL retroviral vector were raised to sexual maturity and egg white from each hen was tested for active β-lactamase (lactamase) at 8 months of age. Of the 57 birds, six had significant levels of lactamase that ranged from 56.3 to 250.0 ng/ml (Table 1, supra). No other hens in this group had detectable levels of lactamase in their egg white, even after incubation of PADAC with the sample for several days. Lactamase was not detectable in egg white from 24 hens that were mock injected and in 42 hens that were transduced with a NLB vector that did not carry the lactamase transgene. Stable lactamase expression was still detectable in the egg white of the six expressing hens six months following the initial assays (Table 1, supra).

Lactamase was detected in the egg white of all six hens by a western blot assay with an anti-β-lactamase antibody. The egg white lactamase was the same size as the bacterially produced, purified lactamase that was used as a standard. The amount detected in egg white by Western analysis was consistent with that determined by the enzymatic assay, indicating that a significant proportion of the egg white lactamase was biologically active. Hen-produced lactamase in egg white stored at 4° C. lost no activity and showed no change in molecular weight even after several months of storage. This observation allowed storage of lactamase-containing eggs for extended periods prior to analysis.

Example 4

Figure 4:
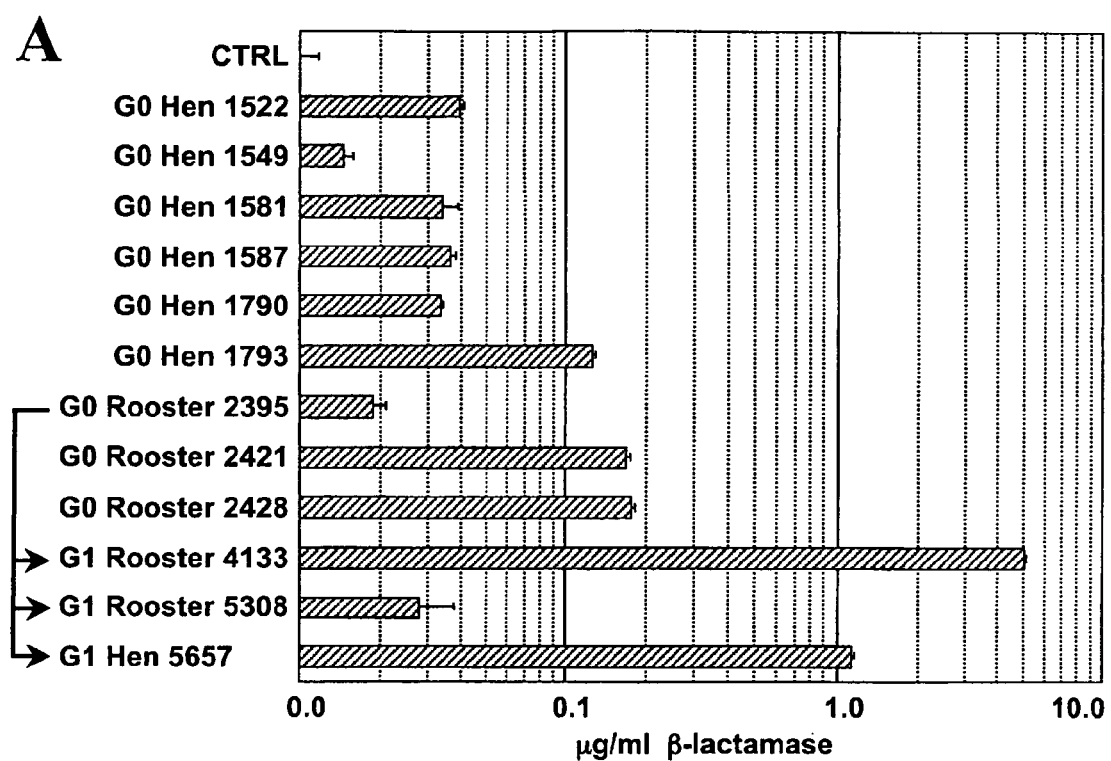
FIGS. 4A and 4B show the amount of β-lactamase (lactamase) in the blood serum of chimeric and transgenic chickens.
Figure 4:
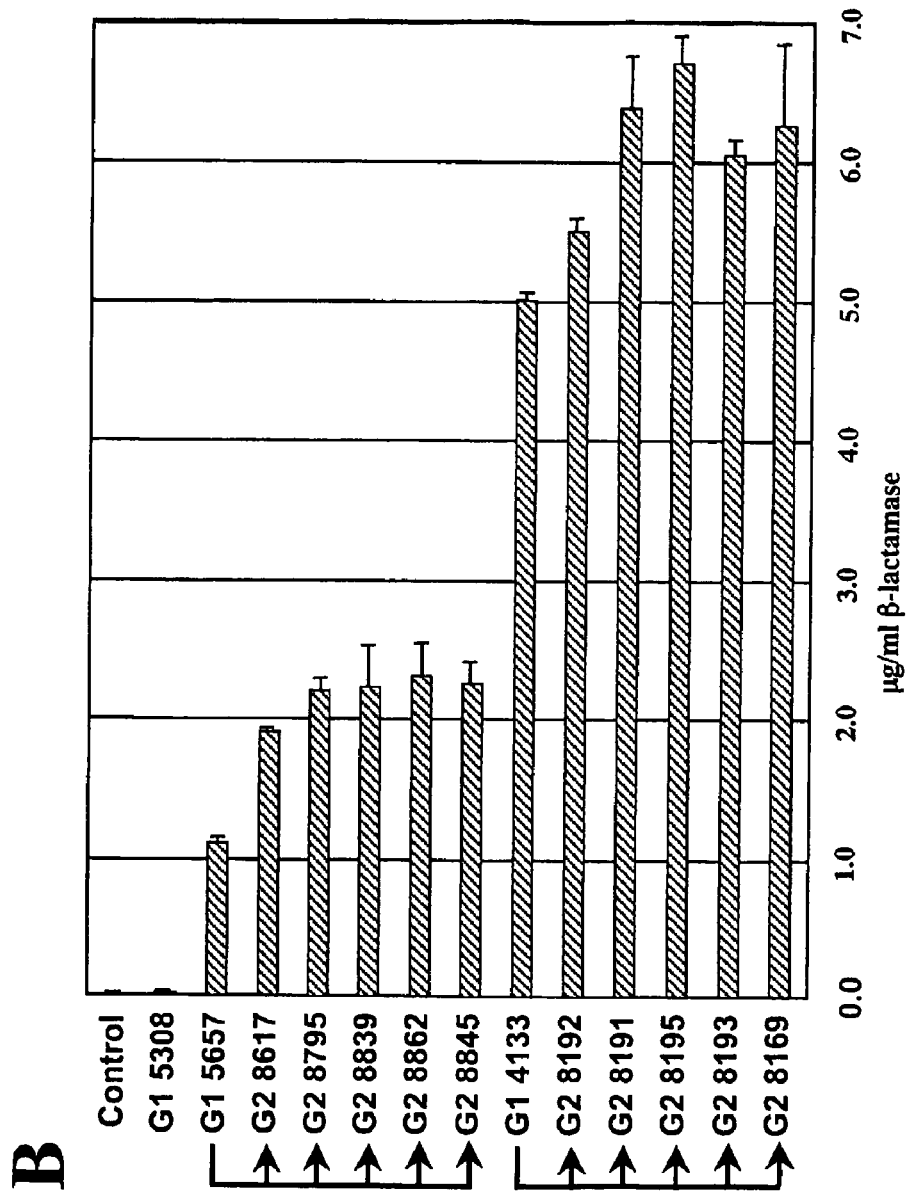

Germline Transmission and Serum Expression of the β-Lactamase Transgene in G1 and G2 Transgenic Chickens DNA was extracted from sperm collected from 56 G0 roosters and three of the 56 birds that harbored significant levels of the transgene in their sperm DNA as determined by quantitative PCR were selected for breeding. These roosters were the same three that had the highest levels of β-lactamase (lactamase) in their blood (roosters 2395, 2421 and 2428). Rooster 2395 gave rise to three G1 transgenic offspring (out of 422 progeny) whereas the other two yielded no transgenic offspring out of 630 total progeny. Southern analysis of blood DNA from each of the three G1 transgenic chickens confirmed that the transgenes were intact and that they were integrated at unique random loci. The serum of the G1 transgenic chicks, 5308, 5657 and 4133, at 6 to 11 weeks post-hatch contained 0.03, 2.0 and 6.0 μg/ml of lactamase, respectively. The levels of lactamase dropped to levels of 0.03, 1.1 and 5.0 μg/ml when the chickens were assayed again at 6 to 7 months of age (FIG. 4A).

Hen 5657 and rooster 4133 were bred to non-transgenic chickens to obtain offspring hemizygous for the transgene. The pedigrees of transgenic chickens bred from rooster 4133 or hen 5657 and the subsequent generations are shown in FIG. 5. Transgenic rooster 5308 was also bred but this bird's progeny exhibited lactamase concentrations that were either very low or not detectable in serum and egg white. Active lactamase concentrations in the serum of randomly selected G2 transgenic chicks were measured at 3 to 90 days post-hatch. Of the five G2 transgenics bred from hen 5657, all had active lactamase at concentrations of 1.9 to 2.3 μg/ml (compared to the parental expression of 1.1 μg/ml, FIG. 4B). All of the samples were collected during the same period of time, thus, the lactamase concentrations in the serum of the offspring were expected to be higher than that of the parent since the concentration in hen 5657 had dropped proportionately as she matured. Similarly, the five randomly selected transgenic chicks bred from rooster 4133 all had serum lactamase concentrations that were similar but higher than that of their parent (FIG. 4B).

Example 5

β-Lactamase Expression in the Egg White of Transgenic Hens

Figure 6:
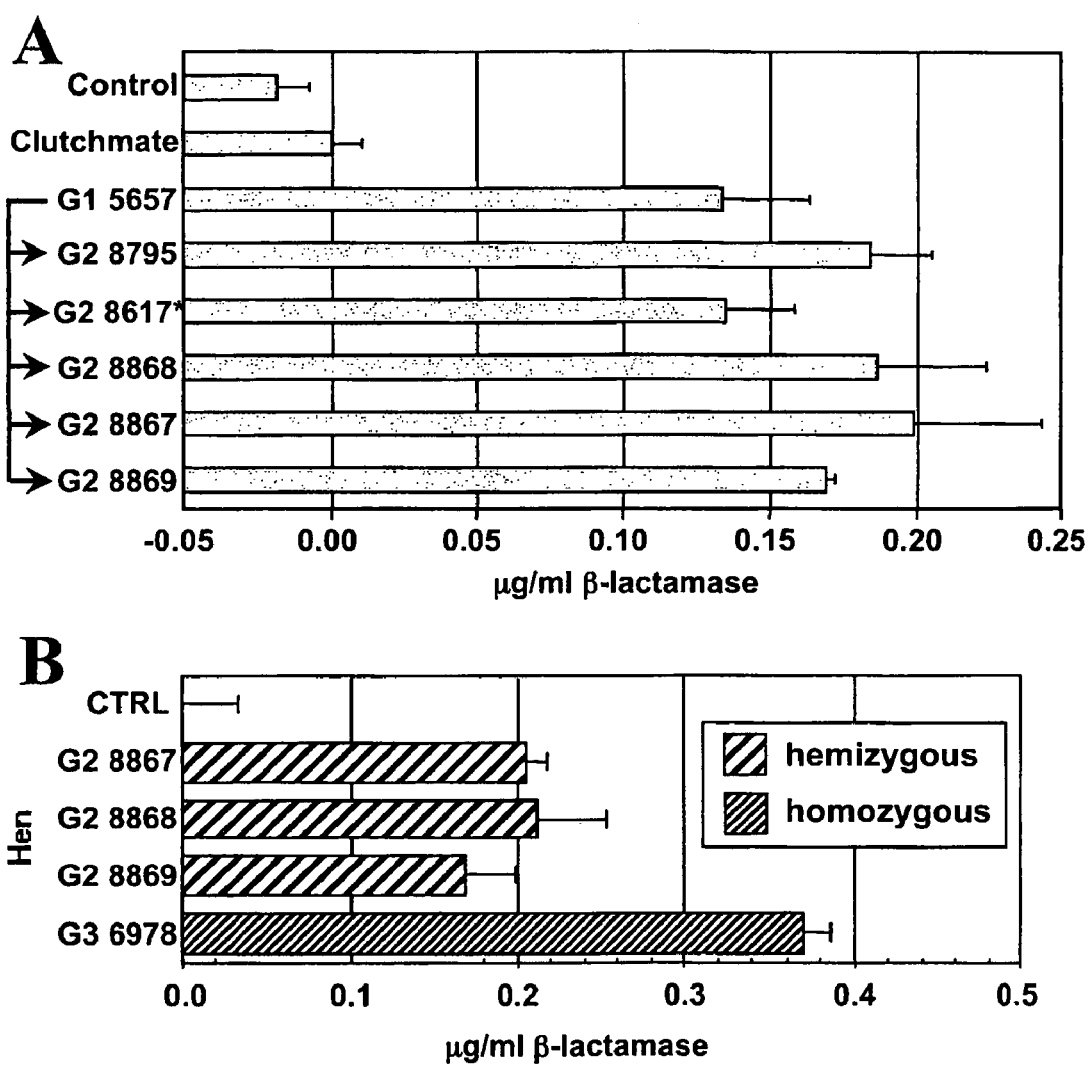
FIG. 6 shows β-lactamase (lactamase) in the egg white of hen 5657 and her offspring.

Eggs from G1 hen 5657 contained 130 ng of active β-lactamase (lactamase) per ml of egg white (FIG. 6A). Lactamase concentrations were higher in the first few eggs laid and then reached a plateau that was stable for at least nine months. Eggs from transgenic hens bred from hen 5657 and a non-transgenic rooster had lactamase concentrations that were similar to their parent (FIG. 6A). Hen 6978 was bred from G2 hen 8617 and sibling G2 rooster 8839 and was homozygous for the transgene as determined by quantitative PCR and Southern analysis. As expected, the concentration of lactamase in the eggs of bird 6978 was nearly two-fold higher than her hemizygous parent (FIG. 6B). No other G3 hens bred from hen 5657 were analyzed because hen 6978 was the only female in her clutch. It is important to note that the eggs from hens 8867, 8868 and 8869 were collected eleven months apart and had similar concentrations of lactamase (FIGS. 6A and 6B), again indicating that the expression levels in the egg white were consistent throughout the lay period.

Figure 7:
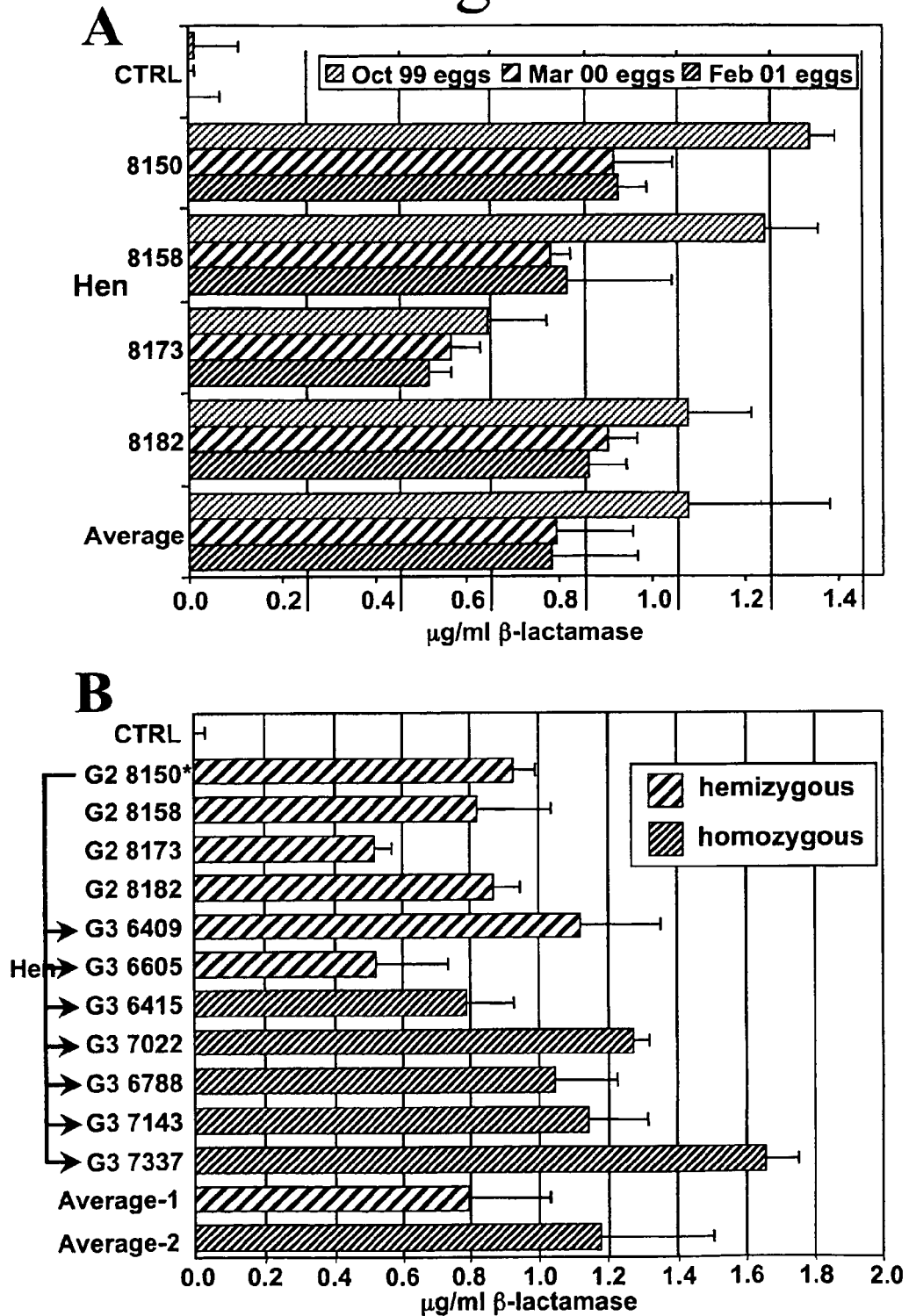
FIG. 7 shows β-lactamase (lactamase) in the eggs of G2 and G3 hens bred from rooster 4133.

Rooster 4133 was bred to non-transgenic hens to obtain hemizygous G2 hens. Of the 15 transgenic hens analyzed, all had lactamase in the egg white at concentrations ranging from 0.47 to 1.34 μg/ml. Four representative hens are shown in FIG. 7A. When assayed 6 months later, the average expression level had dropped from approximately 1.0 μg/ml to 0.8 μg/ml (FIG. 7A). Expression levels were high in the initial eggs and leveled out over several months. After that, the concentrations of lactamase in the eggs remained constant.

G2 hen 8150 and sibling G2 rooster 8191 were crossed to yield hemizygous and homozygous G3 hens. All transgenic G3 hens expressed lactamase in the white of their eggs at concentrations ranging from 0.52 to 1.65 μg/ml (FIG. 7B). The average expression for the G3 hens that were homozygous was 47% higher than those G2 hens and G3 hens that were hemizygous. The amount of lactamase in the eggs from G2 and G3 hens bred from rooster 4133 and his offspring varied significantly (FIGS. 7A and 7B), although the levels in the eggs from any given hen in that group were relatively constant. The average expression of lactamase was expected to double for the homozygous genotype. Western blot analysis confirmed that the transgene was faithfully producing intact lactamase in the eggs of G2 transgenics. The lactamase level detected on a Western blot also correlated closely with that determined by the enzyme activity assay, indicating that a significant portion of the egg white lactamase was bioactive. Thus, retroviral vectors were successfully employed to implement stable and reliable expression of a transgene in chickens.

Deposition of lactamase in the yolk was detectable but lower than that of egg white. Seven G2 or G3 hens of rooster 4133's lineage were analyzed and the concentration in the yolk ranged from 107 to 375 ng/ml or about 20% the concentration in the egg white. There was no correlation between the yolk and egg white lactamase levels of a given hen (Harvey et al., "Expression of exogenous protein in egg white of transgenic chickens" (April 2002) *Nat. Biotechnol.* 20:396-399).

Example 6

Production of Founder Males

For NLB-CMV-BL transduction, freshly laid fertilized White Leghorn eggs were used. Seven to ten microliters of concentrated particles were injected into the subgerminal cavity of windowed eggs and chicks hatched after sealing the window. 546 eggs were injected. Blood DNA was extracted and analyzed for the presence of the transgene using a probe-primer set designed to detect the neo$^r$ gene via the Taqman assay. As can be seen in Table 2 below, approximately 25% of all chicks had detectable levels of transgene in their blood DNA.

TABLE 2

Summary of Transgenesis with the NLB-CMV-BL Vectors

| | Transgene | NLB-CMV-BL |
|---|---|---|
| | Number of injections | 546 |
| | Number of birds hatched (%) | 126 (23.1%) |
| | Number of chicks with transgene in their blood DNA (%) | 36 (28.6%) |
| | Number of males | 56 |
| | Number of males with transgene in their sperm DNA (%) | 3 (5.4%) |
| Production of G1 flock | Number of chicks bred from G0 males | 1026 |
| | Number of G1 transgenics | 3 |
| | Rate of germline transmission | 0.29% |
| Production of G2 flock | Number of chicks bred from G1 transgenics | 120 |
| | Number of G2 transgenics | 61 |
| | Rate of germline transmission | 50.8% |
| | Number of males that transmitted transgene to progeny (%) | 1 (1.8%) |

Example 7

Germline Transmission of the Transgene

Taqman detection of the neo$^r$ gene in sperm DNA was used to identify candidate G0 males for breeding. Three G0 males were identified, wherein each had the NLB-CMV-BL transgene in their sperm DNA at levels that were above background. All G0 males positive for the transgene in their sperm were bred to non-transgenic hens to identify fully transgenic G1 offspring.

For NLB-CMV-BL 1026 chicks were bred, respectively, and three G1 chicks obtained for each transgene (Table 2, supra). All G1 progeny came from the male with the highest level of transgene in his sperm DNA, even though an equivalent number of chicks were bred from each male.

Example 8

Southern Analysis of G1s and G2s

In order to confirm integration and integrity of the inserted vector sequences, Southern blot analysis was performed on DNA from G1 and G2 transgenics. Blood DNA was digested with HindIII and hybridized to a neo$^r$ probe to detect junction fragments created by the internal HindIII site found in the NLB-CMV-BL vector (FIG. 3B) and genomic sites flanking the site of integration. Each of the 3 G1 birds carrying NLB-CMV-BL had a junction fragment of unique size, indicating that the transgene had integrated into three different genomic sites. G1s were bred to non-transgenic hens to obtain hemizygous G2s. As can be seen in Table 2 (supra), 50.8% of offspring from G1 roosters harboring NLB-CMV-BL were transgenic as expected for Mendelian segregation of a single integrated transgene. Southern analysis of HindIII-digested DNA from G2 offspring detected junction fragments similar in size to those originating from their transgenic parents, indicating that the transgene was transmitted intact.

Example 9

Screening for G3 Progeny Homozygous for the Transgene

In order to obtain transgenic chickens homozygous for the transgene, G2 hemizygous birds bearing NLB-CMV-BL integrated at the same site (e.g., progeny of the same G1 male) were crossbred. Two groups were bred: the first was a hen and rooster arising from the G1 4133 male and the second from the G1 5657 hen. The Taqman assay was used to quantitatively detect the neo$^r$ transgene in G3 progeny using a standard curve. The standard curve was constructed using known amounts of genomic DNA from the G1 transgenic 4133 male hemizygous for the transgene as determined by Southern analysis. The standard curve ranged from $10^3$ to $1.6 \times 10^4$ total copies of the transgene or 0.2 to 3.1 transgene copies per diploid genome. Because reaction components were not limited during the exponential phase, amplification was very efficient and gave reproducible values for a given copy number. There was a reproducible, one-cycle difference between each standard curve differing 2-fold in copy number.

In order to determine the number of transgene alleles in the G3 offspring, DNAs were amplified and compared to the standards. DNA from non-transgenics did not amplify. Birds homozygous for the transgenic allele gave rise to plots initiating the amplification one cycle earlier than those hemizygous for the allele. The sequence detection program was able to calculate the number of alleles in an unknown DNA sample based on the standard curve and the cycle threshold (Ct) at which a sample's amplification plot exhibited a significant rise. The data are shown in Table 3 below.

In order to confirm Taqman copy number analysis, DNA of selected birds was analyzed by Southern blotting using PstI-digested DNA and a probe complementary to the neo$^r$ gene to detect a 0.9 kb fragment. Detection of a small fragment was chosen since transfer of smaller DNAs from gel to membrane is more quantitative. The signal intensity of the 0.9 kb band corresponded well to the copy number of G3 transgenic birds as determined by the Taqman assay. The copy numbers of an additional eighteen G3 transgenic birds analyzed by Southern blotting were also consistent with that determined by Taqman. A total of 33 progeny were analyzed for the 4133 lineage, of which 9 (27.3%) were non-transgenic, 16 (48.5%) were hemizygous and 8 (24.2%) were homozygous. A total of 10 progeny were analyzed for the 5657 lineage, of which 5 (50.0%) were non-transgenic, 1 (10.0%) was hemizygous and 4 (40.0%) were homozygous. The observed ratio of non-transgenics, hemizygotes and homozygotes for the 4133 lineage G3 progeny was not statistically different from the expected 1:2:1 ratio as determined by the $\chi^2$ test ($P \leq 0.05$). Progeny of the 5657 lineage did not have the expected distribution but this could have been due to the low number of progeny tested (Harvey et al., "Consistent production of transgenic chickens using replication deficient retroviral vectors and high-throughput screening procedures" (February 2002) *Poultry Science* 81:202-212).

TABLE 3

Determination of Transgene Copy Number in G3 Offspring Bred from G2 Transgenics

| G1 Parent | Band No. (Std. No. or NTC[1]) | Ct[2] | Mean Total Copy Number | Standard Deviation | Copies per Diploid Genome[3] |
|---|---|---|---|---|---|
| NA[4] | 4133 | 27.3 | 3,975 | 145.7 | 1 |
| 4133 | 6792 | 40.0 | 0 | 0.0 | 0 |
| 5657 | 6977 | 25.9 | 10,510 | 587.0 | 2 |
| 5657 | 6978 | 25.8 | 10,401 | 505.1 | 2 |
| 4133 | 7020 | 26.7 | 6,064 | 443.1 | 1 |
| 4133 | 7021 | 26.8 | 5,239 | 133.8 | 1 |
| 4133 | 7022 | 26.1 | 9,096 | 352.3 | 2 |
| 4133 | 7023 | 26.8 | 5,424 | 55.7 | 1 |
| 4133 | 7024 | 26.9 | 4,820 | 110.1 | 1 |
| 5657 | 7110 | 26.4 | 8,092 | 1037.5 | 2 |
| 5657 | 7111 | 30.4 | 403 | 46.3 | 0 |
| 5657 | 7112 | 33.2 | 60 | 6.1 | 0 |
| 4133 | 7142 | 26.5 | 6,023 | 367.6 | 1 |
| 4133 | 7143 | 25.9 | 9,474 | 569.8 | 2 |
| 4133 | 7144 | 25.7 | 12,420 | 807.7 | 2 |
| 4133 | 7338 | 27.2 | 4,246 | 201.7 | 1 |
| 5657 | 7407 | 37.7 | 1 | 1.0 | 0 |
| NA | (std1) | 29.1 | 1,000 | 0.0 | 0.2 |
| NA | (std2) | 28.1 | 2,000 | 0.0 | 0.4 |
| NA | (std3) | 27.1 | 4,000 | 0.0 | 0.8 |
| NA | (std4) | 26.2 | 8,000 | 0.0 | 1.6 |
| NA | (std5) | 25.3 | 16,000 | 0.0 | 3.1 |
| NA | (NTC) | 39.8 | −1 | 0.0 | 0.0 |

[1]Std. No.: standard number; NTC: no template control.
[2]Ct: cycle threshold; cycle at which a sample's fluorescence exhibited a significant increase above background.
[3]Copies per diploid genome were determined by dividing the mean by 5100 and rounding to the nearest first decimal place.
[4]NA: not applicable.

Example 10

Vector Construction for pNLB-MDOT-EPO Vector

Following the teachings of Example 1 (Vector Construction) of the specification, an pNLB-MDOT-EPO vector was created, substituting an EPO encoding sequence for the BL encoding sequence (FIG. 8B). Instead of using the CMV promoter MDOT was used (FIG. 13). MDOT is a synthetic promoter which contains elements from both the ovomucoid (MD) and ovotransferrin (OT) promoter. (pNLB-MDOT-EPO vector, a.k.a. pAVIJCR-A145.27.2.2).

The DNA sequence for human EPO based on hen oviduct optimized codon usage was created using the BACK-TRANSLATE program of the Wisconsin Package, version 9.1 (Genetics Computer Group, Inc., Madison, Wis.) with a codon usage table compiled from the chicken (Gallus gallus) ovalbumin, lysozyme, ovomucoid, and ovotransferrin proteins. The DNA sequence was synthesized and cloned into the 3' overhang T's of pCRII-TOPO (Invitrogen) by Integrated DNA Technologies, Coralville, Iowa, on a contractual basis. The EPO coding sequence was then removed from pEpoMM with Hind III and Fse I, purified from a 0.8% agarose-TAE Gel, and ligated to Hind III and Fse I digested, alkaline phosphatase-treated pCMV-IFNMM. The resulting plasmid was pAVIJCR-A137.43.2.2 which contained the EPO coding sequence controlled by the cytomegalovirus immediate early promoter/enhancer and SV40 polyA site. The plasmid pAVIJCR-A137.43.2.2 was digested with Nco I and Fse I and the appropriate fragment ligated to an Nco I and Fse I-digested fragment of pMDOTIFN to obtain pAVIJCR-A137.87.2.1 which contained EPO driven by the MDOT promoter. In order to clone the EPO coding sequence controlled by the MDOT promoter into the NLB retroviral plasmid, the plasmids pALVMDOTIFN and pAVIJCR-A137.87.2.1 were digested with Kpn I and Fse I. Appropriate DNA fragments were purified on a 0.8% agarose-TAE gel, then ligated and transformed into DH5α cells. The resulting plasmid was pNLB-MDOT-EPO (a.k.a. pAVIJCR-A145.27.2.2).

Example 11

Production of Transgenic Chickens and Fully Transgenic G1 Chickens Expressing EPO Production of NLB-MDOT-EPO transduction particles were performed as described for NLB-CMV-BL (see Example 2). Approximately 300 White Leghorn eggs were windowed according to the Speksnijder procedure (U.S. Pat. No. 5,897,998), then injected with ~7×10⁴ transducing particles per egg. Eggs hatched 21 days after injection, and human EPO levels were measured by EPO ELISA from serum samples collected from chicks one week after hatch.

In order to screen for G$_0$ roosters which contained the EPO transgene in their sperm, DNA was extracted from rooster sperm samples by Chelex-100 extraction (Walsh et al., 1991). DNA samples were then subjected to Taqman™ analysis on a 7700 Sequence Detector (Perkin Elmer) using the "neo for-1" (5'-TGGATTGCACGCAGGTTCT-3') and "neo rev-1" (5'-GTGCCCAGTCATAGCCGAAT-3') primers and FAM labeled NEO-PROBE1 (5'-CCTCTCCAC-CCAAGCGGCCG-3') to detect the transgene. Eight G$_0$ roosters with the highest levels of the transgene in their sperm samples were bred to nontransgenic SPAFAS (White Leghorn) hens by artificial insemination. Blood DNA samples were screened for the presence of the transgene by Taqman™ analysis as described above.

Out of 1,054 offspring, 16 chicks were found to be transgenic (G1 avians). Chick serum was tested for the presence of human EPO by EPO ELISA, and EPO was present at ~70 nanogram/ml (ng/ml). Egg white in eggs from G1 hens was also tested for the presence of human EPO by EPO ELISA and found to contain human EPO at ~70 ng/ml. The EPO present in eggs (i.e., derived from the optimized coding sequence of human EPO) was found to be biologically active when tested on a human EPO responsive cell line (HCD57 murine erythroid cells) in a cell culture assay.

Example 12

Vector Construction for pNLB-CMV-IFN

Following the teachings of Example 1, a pNLB-CMV-IFN vector was created (FIG. 8A), substituting an IFN encoding sequence for the BL encoding sequence of Example 1.

An optimized coding sequence was created, wherein the most frequently used codons for each particular amino acid found in the egg white proteins ovalbumin, lysozyme, ovomucoid, and ovotransferrin were used in the design of the optimized human IFN-α 2b coding sequence that was inserted into vectors of the instant invention. More specifically, the DNA sequence for optimized human IFN-α 2b is based on the hen oviduct optimized codon usage and was created using the BACKTRANSLATE program of the Wisconsin Package, Version 9.1 (Genetics Computer Group Inc., Madison, Wis.) with a codon usage table compiled from the chicken (Gallus gallus) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU was used as the codon for the majority of alanines in the optimized human IFN-α 2b coding sequence. The vectors containing the gene for optimized human IFN-α 2b were used to create transgenic avians that express transgenic poultry derived interferon-α 2b (TPD IFN-α 2b) in their tissues and eggs.

The template and primer oligonucleotides listed in Table 4 below were amplified by PCR with Pfu polymerase (Stratagene, La Jolla, Calif.) using 20 cycles of 94° C. for 1 min.; 50° C. for 30 sec.; and 72° C. for 1 min. and 10 sec. PCR products were purified from a 12% polyacrylamide-TBE gel by the "crush and soak" method (Maniatis et al. 1982), then combined as templates in an amplification reaction using only IFN-1 and IFN-8 as primers (see Table 4). The resulting PCR product was digested with Hind III and Xba I and gel purified from a 2% agarose-TAE gel, then ligated into Hind III and Xba I digested, alkaline phosphatase-treated pBluescript KS (Stratagene), resulting in the plasmid pBluKSP-IFNMagMax. Both strands were sequenced by cycle sequencing on an ABI PRISM 377 DNA Sequencer (Perkin-Elmer, Foster City, Calif.) using universal T7 or T3 primers. Mutations in pBluKSP-IFN derived from the original oligonucleotide templates were corrected by site-directed mutagenesis with the Transformer Site-Directed Mutagenesis Kit (Clontech, Palo Alto, Calif.). The IFN coding sequence was then removed from the corrected pBluKSP-IFN with Hind III and Xba 1, purified from a 0.8% agarose-TAE Gel, and ligated to Hind III and Xba I digested, alkaline phosphatase-treated pCMV-BetaLa-3B-dH. The resulting plasmid was pCMV-IFN which contained an IFN coding sequence controlled by the cytomegalovirus immediate early promoter/enhancer and SV40 polyA site. In order to clone the IFN coding sequence controlled by the CMV promoter/enhancer into the NLB retroviral plasmid, pCMV-IFN was first digested with ClaI and XbaI, then both ends were filled in with Klenow fragment of DNA polymerase (New England BioLabs, Beverly, Mass.). pNLB-adapter was digested with NdeI and KpnI, and both ends were made blunt by T4 DNA polymerase (New England BioLabs). Appropriate DNA fragments were purified on a 0.8% agarose-TAE gel, then ligated and transformed into DH5α cells. The resulting plasmid was pNLB-adapter-CMV-IFN. This plasmid was then digested with MluI and partially digested with BlpI and the appropriate fragment was gel purified. pNLB-CMV-EGFP was digested with MluI and BlpI, then alkaline-phosphatase treated and gel purified. The MluI/BlpI partial fragment of pNLB-adapter-CMV-IFN was ligated to the large fragment derived from the MluI/BlpI digest of pNLB-CMV-EGFP creating pNLB-CMV-IFN.

TABLE 4

Oligonucleotides used for IFN Gene Synthesis

| Template | Sequence of Template | Primer 1 | Sequence of Primer 1 | Primer 2 | Sequence of Primer 2 |
|---|---|---|---|---|---|
| INF-A | 5'ATGGCTTTGACCTTTGCCTTACTGGTGGCTCTCCTGGTGCTGAGCTGCAAGAGCAGCTGCTCTGTGGGCTGCGATCTGCCTCA3' | IFN-1 | 5'CCCAAGCTTTCACCATGGCTTTGACCTTTGCCTT3' | IFN-2 | 5'CTGTGGGTCTGAGGCAGAT3' |
| IFN-B | 5'GACCCACAGCCTGGGCAGCAGGAGGACCCTGATGCTGCTGGCTCAGATGAGGAGAATCAGCCTGTTTAGCTGCCTGAAGGATAGGCACGATTTTGGCTTT3' | IFN-2b | 5'ATCTGCCTCAGACCCACAG3' | IFN-3b | 5'AACTCCTCTTGAGGAAAGCCAAAATC3' |
| IFN-C | 5'CTCAAGAGGAGTTTGGCAACCAGTTTCAGAAGGCTGAGACCATCCCTGTGCTGCACGAGATG3' | IFN-3c | 5'GATTTTGGCTTTCCTCAAGAGGAGTT3' | IFN-4 | 5'ATCTGCTGGATCATCTCGTGC3' |
| IFN-D | 5'ATCCAGCAGATCTTTAACCTGTTTAGCACCAAGGATAGCAGCGCTGCTTGGGATGAGACCCTGCTGGATAAGTTTACACCGAGCTGTACCAGCA3' | IFN-4b | 5'GCACGAGATGATCCAGCAGAT3' | IFN-5 | 5'ATCGTTCAGCTGCTGGTACA3' |
| IFN-E | 5'GCTGAACGATCTGGAGGCTTGCGTGATCCAGGGCGTGGGCGTGACCGAGACCCCTCTGATGAAGGAGGATAGCATCCT3' | IFN-5b | 5'TGTACCAGCAGCTGAACGAT3' | IFN-6 | 5'CCTCACAGCCAGGATGCTAT3' |

TABLE 4-continued Oligonucleotides used for IFN Gene Synthesis

| Template | Sequence of Template | Primer 1 | Sequence of Primer 1 | Primer 2 | Sequence of Primer 2 |
|---|---|---|---|---|---|
| IFN-F | 5'GGCTGTGAGGAAGTACTTTCAGAGGATCACCCTGTACCTGAAGGAGAAGAAGTACAGCCCTTGCGCTTGGGAAGTCGTGAGGG3' | IFN-6b | 5'ATAGCATCCTGGCTGTGAGG3' | IFN-7 | 5'ATGATCTCAGCCCTCACGAC3' |
| IFN-G | 5'CTGAGATCATGAGGAGCTTTAGCCTGAGCACCAACCTGCAAGAGAGCTTGAGGTCTAAGGAGTAA3' | IFN-7b | 5'GTCGTGAGGGCTGAGATCAT3' | IFN-8 | 5'TGCTCTAGACTTTTTACTCCTTAGACCTCAAGCTCT3' |

Example 13

Production of Transgenic Chickens and Fully Transgenic G1 Chickens Expressing IFN Transduction particles of pNLB-CMV-IFN were produced following the procedures of Example 2. Approximately 300 White Leghorn (strain Line 0) eggs were windowed according to the Speksnijder procedure (U.S. Pat. No. 5,897,998), then injected with ~7×10$^4$ transducing particles per egg. Eggs hatched 21 days after injection, and human IFN levels were measured by IFN ELISA from serum samples collected from chicks one week after hatch.

In order to screen for G$_0$ roosters which contained the IFN transgene in their sperm, DNA was extracted from rooster sperm samples by Chelex-100 extraction (Walsh et al., 1991). DNA samples were then subjected to Taqman™ analysis on a 7700 Sequence Detector (Perkin Elmer) using the "neo for-1" (5'-TGGATTGCACGCAGGTTCT-3') and "neo rev-1" (5'-GTGCCCAGTCATAGCCGAAT-3') primers and FAM labeled NEO-PROBE1 (5'-CCTCTCCAC-CCAAGCGGCCG-3') to detect the transgene. Three G$_0$ roosters with the highest levels of the transgene in their sperm samples were bred to nontransgenic SPAFAS (White Leghorn) hens by artificial insemination.

Blood DNA samples were screened for the presence of the transgene by Taqman™ analysis as described above. Out of 1,597 offspring, one rooster was found to be transgenic (a.k.a. "Alphie"). Alphie's serum was tested for the presence of hIFN by hIFN ELISA, and hIFN was present at 200 ng/ml.

Alphie's sperm was used for artificial insemination of nontransgenic SPAFAS (White Leghorn) hens. 106 out of 202 (~52%) offspring contained the transgene as detected by Taqman™ analysis. These breeding results followed a Mendelian inheritance pattern and indicated that Alphie is transgenic.

Example 14

Carbohydrate Analysis of Transgenic Poultry Derived Interferon-α 2b (TPD IFN-α 2b)

Experimental evidence revealed a new glycosylation pattern in interferon-α 2b derived from avians (i.e., TPD IFN-α 2b). TPD IFN-α 2b was found to contain two new glyco forms (bands 4 and 5 are α-Gal extended disaccharides; see FIG. 9) not normally seen in human peripheral blood leukocyte derived interferon-α 2b (PBL IFN-α 2b) or natural human interferon-α 2b (natural hIFN). TPD IFN-α 2b was also found to contain O-linked carbohydrate structures that are similar to human PBL IFN-α 2b and was more efficiently produced in chickens then the human form.

The coding sequence for human IFN-α 2b was optimized (Example 12, supra) resulting in a recombinant IFN-α 2b coding sequence. TPD IFN-α 2b was then produced in chickens (Example 13, supra). A carbohydrate analysis, including a monosaccharide analysis and FACE analysis, revealed the sugar make-up or novel glycosylation pattern of the protein. As such, TPD IFN-α 2b showed the following monosaccharide residues: N-Acetyl-Galactosamine (NAc-Gal), Galactose (Gal), N-Acetyl-Glucosamine (NAcGlu), and Sialic acid (SA). No N-linked glycosylation was found in TPD IFN-α 2b. Instead, TPD IFN-α 2b was found to be O-glycosylated at Thr-106. This type of glycosylation is similar to human IFN-α 2, wherein the Thr residue at position 106 is unique to IFN-α 2. In addition, TPD IFN-α 2b was found to have no mannose residues. A FACE analysis revealed 6 bands (FIG. 9) that represent various sugar residues, wherein bands 1, 2 and 3 are un-sialyated, mono-sialyated, and di-sialyated, respectively (FIG. 10). The sialic acid (SA) linkage is alpha 2-3 to Galactose (Gal) and alpha 2-6 to N-Acetyl-Galactosamine (NAcGal). Band 6 represents an un-sialyated tetrasaccharide. Bands 4 and 5 were found to be alpha-Galactose (alpha-Gal) extended disaccharides that are not seen in human PBL IFN-α 2b. FIG. 10 shows the comparison of TPD IFN-α 2b (egg white hIFN) and human PBL IFN-α 2b (natural hIFN). Minor bands were present between bands 3 and 4 and between bands 4 and 5 in TPD IFN-α 2b (vide infra).

The protein was found to be O-glycosylated at Thr-106 with specific residues, such as:

(i)
    Gal-NAcGal- (ii)
    SA-Gal-NAcGal- (iii)

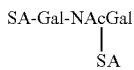

(iv)

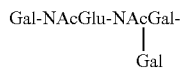

(v)

Gal-Gal-NAcGal- (vi)

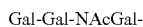

wherein Gal=Galactose,

NAcGal=N-Acetyl-Galactosamine,

NAcGlu=N-Acetyl-Glucosamine, and

SA=Sialic Acid.

The percentages were as follows:

(i)

Gal-NAcGal- is about 20%

(ii)

SA-Gal-NAcGal- is about 29%

(iii)

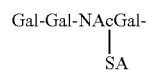

(iv)

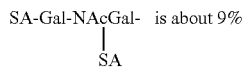

(v)

Gal-Gal-NAcGal- is about 7%

(vi)

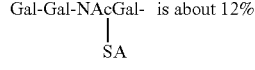

Minor bands were present between bands 3 and 4 and between bands 4 and 5 which account for about 17% in TPD IFN-α 2b.

Example 15

Expression of MAbs from Plasmid Transfection and Retroviral Transduction using the EMCV IRES in Avian Cells The light chain (LC) and heavy chain (HC) of a human monoclonal antibody were expressed from a single vector, pCMV-LC-emcvIRES-HC, by placement of an IRES from the encephalomyocarditis virus (EMCV) (see also Jang et al. (1988) "A segment of the 5' nontranslated region of encephalomyocarditis virus RNA directs internal entry of ribosomes during in vitro translation" *J. Virol.* 62:2636-2643) between the LC and HC coding sequences. Transcription was driven by the CMV promoter.

In order to test expression of monoclonal antibodies from two separate vectors, the LC or HC linked to the CMV promoter were cotransfected into LMH/2a cells, an estrogen-responsive, chicken hepatocyte cell line (see also Binder et al. (1990) "Expression of endogenous and transfected apolipoprotein II and vitellogenin II genes in an estrogen responsive chicken liver cell line" *Mol. Endocrinol.* 4:201-208). Contransfection of pCMV-LC and pCMV-HC resulted in 392 ng/ml of MAbs determined by a MAB ELISA whereas transfection of pCMV-LC-emcvIRES-HC resulted in 185 ng/ml of MAb.

The CMV-LC-emcv-HC cassette was inserted in a retroviral vector based on the Moloney murine leukemia virus (MLV), creating pL-CMV-LC-emcvIRES-HC-RN-BG. LMH cells (see also Kawaguchi et al. (1987) "Establishment and characterization of a chicken hepatocellular carcinoma cell line, LMH" *Cancer Res.* 47:4460-4464), the parent line of LMH/2a, were used as target cells because they are not neomycin resistant. LMH cells were transduced with the L-CMV-LC-emcvIRES-HC-RN-BG retroviral vector and selected with neomycin and passaged for several weeks. LMH cells were separately transduced and neomycin selected with the parent MLV vector, LXRN. Media from LXRN cells were negative for MAb, whereas media from the L-CMV-LC-emcvIRES-HC-RN-BG-transduced cells contained 22 ng/ml of MAb.

All documents (e.g., U.S. patents, U.S. patent applications, publications) cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A composition comprising human interferon-α derived from a chicken wherein the interferon is glycosylated with:

Gal-NAcGal-,

SA-Gal-NAcGal-,

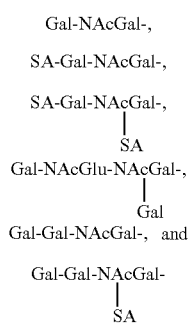

Gal-Gal-NAcGal-, and

Gal-Gal-NAcGal-
|
SA wherein Gal=Galactose,
NAcGal=N-Acetyl-Galactosamine,
NAcGlu=N-Acetyl-Glucosamine, and
SA=Sialic Acid.

2. A pharmaceutical composition comprising the interferon of claim 1.

3. The pharmaceutical composition of claim 2 wherein the interferon is glycosylated as follows:

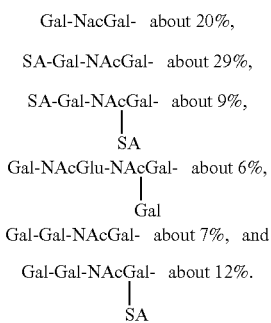

4. The interferon of claim 1 wherein the interferon is interferon α2.

5. The interferon of claim 1 wherein the glycosylation is O-linked.

6. The interferon of claim 5 wherein the O-linked glycosylation is at threonine-106.

7. The interferon of claim 1 wherein the interferon comprises SEQ ID NO: 30.

8. A composition comprising human interferon-α derived from a chicken glycosylated with:

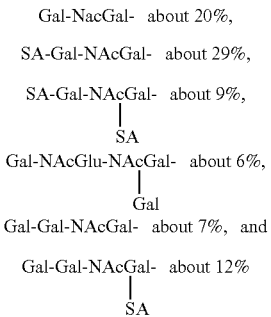

wherein Gal=Galactose,
NAcGal=N-Acetyl-Galactosamine,
NAcGlu=N-Acetyl-Glucosamine, and
SA=Sialic Acid.

9. The interferon of claim 8 wherein the interferon is interferon α2.

10. The interferon of claim 8 wherein the glycosylation is O-linked.

11. The interferon of claim 10 wherein the O-linked glycosylation is at threonine-106.

12. The interferon of claim 8 wherein the interferon comprises SEQ ID NO: 30.

13. A human interferon-α comprising a chicken derived glycosylation pattern wherein the glycosylation is not the same as a human interferon-α.

14. The interferon of claim 13 wherein the interferon is interferon α2.

15. The interferon of claim 13 wherein the glycosylation is O-linked.

16. The interferon of claim 15 wherein the O-linked glycosylation is at threonine-106.

17. The interferon of claim 13 wherein the glycosyaltion is produced in a tubular gland cell of the chicken.

18. The interferon of claim 13 wherein the interferon comprises SEQ ID NO: 30.

* * * * *

UNITED STATES PATENT AND TRADEMARK OFFICE
CERTIFICATE OF CORRECTION

| | | Page 1 of 1 |
|---|---|---|
| PATENT NO. | : 7,338,654 B2 | |
| APPLICATION NO. | : 11/370555 | |
| DATED | : March 4, 2008 | |
| INVENTOR(S) | : Ivarie et al. | |

It is certified that error appears in the above-identified patent and that said Letters Patent is hereby corrected as shown below:

Column 1, line 15: insert

--GOVERNMENT RIGHTS STATEMENT

This invention was funded, at least in part, with a government grant from the Department of Commerce, NIST-ATP Grant Number 70NANB8H4049. The United States Government may therefore have certain rights in this invention.--

Signed and Sealed this
Fifth Day of July, 2011

David J. Kappos
*Director of the United States Patent and Trademark Office*

SEQUENCE LISTING

```
<160> NUMBER OF SEQ ID NOS: 31

<210> SEQ ID NO 1
<211> LENGTH: 579
<212> TYPE: DNA
<213> ORGANISM: Artificial
<220> FEATURE:
<223> OTHER INFORMATION: synthetic optimized human erythropoietin
      (EPO) sequence, recombinant transgenic poultry derived
      erythropoietin (TPD EPO) cDNA
```

-continued

```
<400> SEQUENCE: 1
atgggcgtgc acgagtgccc tgcttggctg tggctgctct tgagcctgct cagcctgcct      60
ctgggcctgc ctgtgctggg cgctcctcca aggctgatct gcgatagcag ggtgctggag     120
aggtacctgc tggaggctaa ggaggctgag aacatcacca ccggctgcgc tgagcactgc     180
agcctgaacg agaacatcac cgtgcctgat accaaggtga actttacgc ttggaagagg      240 atggaggtgg gccagcaggc tgtggaggtg tggcagggcc tggctctgct gagcgaggct     300
gtgctgaggg gccaggctct gctggtgaac agctctcagc cttgggagcc tctgcagctg     360
cacgtggata aggctgtgag cggcctgaga agcctgacca ccctgctgag ggctctgggc     420
gctcagaagg aggctatcag ccctccagat gctgcaagcg ctgcccctct gaggaccatc     480
accgctgata cctttaggaa gctgtttagg gtgtacagca ctttctgag gggcaagctg      540 aagctgtaca ccggcgaggc ttgcaggacc ggcgatagg                            579

<210> SEQ ID NO 2
<211> LENGTH: 193
<212> TYPE: PRT
<213> ORGANISM: Artificial
<220> FEATURE:
<223> OTHER INFORMATION: synthetic optimized human erythropoietin
      (EPO) sequence, recombinant transgenic poultry derived
      erythropoietin (TPD EPO) cDNA

<400> SEQUENCE: 2

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
                20                  25                  30

Ile Cys Asp Ser Arg Val Leu Glu Arg Tyr Leu Leu Glu Ala Lys Glu
            35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
                100                 105                 110

Gln Pro Trp Glu Pro Leu Gln Leu His Val Asp Lys Ala Val Ser Gly
            115                 120                 125

Leu Arg Ser Leu Thr Thr Leu Leu Arg Ala Leu Arg Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg

<210> SEQ ID NO 3
<211> LENGTH: 19
<212> TYPE: DNA
<213> ORGANISM: Artificial
<220> FEATURE:
```

```
<223> OTHER INFORMATION: "neo for-1" primer

<400> SEQUENCE: 3
tggattgcac gcaggttct                                                   19

<210> SEQ ID NO 4
<211> LENGTH: 20
<212> TYPE: DNA
<213> ORGANISM: Artificial
<220> FEATURE:
<223> OTHER INFORMATION: "neo rev-1" primer

<400> SEQUENCE: 4
gtgcccagtc atagccgaat                                                  20

<210> SEQ ID NO 5
<211> LENGTH: 20
<212> TYPE: DNA
<213> ORGANISM: Artificial
<220> FEATURE:
<223> OTHER INFORMATION: FAM labeled NEO-PROBE1

<400> SEQUENCE: 5
cctctccacc caagcggccg                                                  20

<210> SEQ ID NO 6
<211> LENGTH: 83
<212> TYPE: DNA
<213> ORGANISM: Artificial
<220> FEATURE:
<223> OTHER INFORMATION: IFN-A template oligonucleotide

<400> SEQUENCE: 6
atggctttga cctttgcctt actggtggct ctcctggtgc tgagctgcaa gagcagctgc      60
tctgtgggct gcgatctgcc tca                                              83

<210> SEQ ID NO 7
<211> LENGTH: 34
<212> TYPE: DNA
<213> ORGANISM: Artificial
<220> FEATURE:
<223> OTHER INFORMATION: IFN-1 primer 1 oligonucleotide

<400> SEQUENCE: 7
cccaagcttt caccatggct ttgacctttg cctt                                  34

<210> SEQ ID NO 8
<211> LENGTH: 19
<212> TYPE: DNA
<213> ORGANISM: Artificial
<220> FEATURE:
<223> OTHER INFORMATION: IFN-2 primer 2 oligonucleotide

<400> SEQUENCE: 8
ctgtgggtct gaggcagat                                                   19

<210> SEQ ID NO 9
<211> LENGTH: 100
<212> TYPE: DNA
<213> ORGANISM: Artificial
<220> FEATURE:
<223> OTHER INFORMATION: IFN-B template oligonucleotide

<400> SEQUENCE: 9
gacccacagc ctgggcagca ggaggaccct gatgctgctg gctcagatga ggagaatcag      60
```
cctgtttagc tgcctgaagg ataggcacga ttttggcttt                                100

<210> SEQ ID NO 10
<211> LENGTH: 19
<212> TYPE: DNA
<213> ORGANISM: Artificial
<220> FEATURE:
<223> OTHER INFORMATION: IFN-2b primer 1 oligonucleotide

<400> SEQUENCE: 10
atctgcctca gacccacag                                                       19

<210> SEQ ID NO 11
<211> LENGTH: 26
<212> TYPE: DNA
<213> ORGANISM: Artificial
<220> FEATURE:
<223> OTHER INFORMATION: IFN-3b primer 2 oligonucleotide

<400> SEQUENCE: 11
aactcctctt gaggaaagcc aaaatc                                               26

<210> SEQ ID NO 12
<211> LENGTH: 62
<212> TYPE: DNA
<213> ORGANISM: Artificial
<220> FEATURE:
<223> OTHER INFORMATION: IFN-C template oligonucleotide

<400> SEQUENCE: 12
ctcaagagga gtttggcaac cagtttcaga aggctgagac catccctgtg ctgcacgaga           60
tg                                                                         62

<210> SEQ ID NO 13
<211> LENGTH: 26
<212> TYPE: DNA
<213> ORGANISM: Artificial
<220> FEATURE:
<223> OTHER INFORMATION: IFN-3c primer 1 oligonucleotide

<400> SEQUENCE: 13
gattttggct ttcctcaaga ggagtt                                               26

<210> SEQ ID NO 14
<211> LENGTH: 21
<212> TYPE: DNA
<213> ORGANISM: Artificial
<220> FEATURE:
<223> OTHER INFORMATION: IFN-4 primer 2 oligonucleotide

<400> SEQUENCE: 14
atctgctgga tcatctcgtg c                                                    21

<210> SEQ ID NO 15
<211> LENGTH: 95
<212> TYPE: DNA
<213> ORGANISM: Artificial
<220> FEATURE:
<223> OTHER INFORMATION: IFN-D template oligonucleotide

<400> SEQUENCE: 15
atccagcaga tctttaacct gtttagcacc aaggatagca gcgctgcttg ggatgagacc           60
ctgctggata agtttacac cgagctgtac cagca                                      95

```
<210> SEQ ID NO 16
<211> LENGTH: 21
<212> TYPE: DNA
<213> ORGANISM: Artificial
<220> FEATURE:
<223> OTHER INFORMATION: IFN-4b primer 1 oligonucleotide

<400> SEQUENCE: 16
gcacgagatg atccagcaga t                                               21

<210> SEQ ID NO 17
<211> LENGTH: 20
<212> TYPE: DNA
<213> ORGANISM: Artificial
<220> FEATURE:
<223> OTHER INFORMATION: IFN-5 primer 2 oligonucleotide

<400> SEQUENCE: 17
atcgttcagc tgctggtaca                                                 20

<210> SEQ ID NO 18
<211> LENGTH: 78
<212> TYPE: DNA
<213> ORGANISM: Artificial
<220> FEATURE:
<223> OTHER INFORMATION: IFN-E template oligonucleotide

<400> SEQUENCE: 18
gctgaacgat ctggaggctt gcgtgatcca gggcgtgggc gtgaccgaga cccctctgat    60
gaaggaggat agcatcct                                                   78

<210> SEQ ID NO 19
<211> LENGTH: 20
<212> TYPE: DNA
<213> ORGANISM: Artificial
<220> FEATURE:
<223> OTHER INFORMATION: IFN-5b primer 1 oligonucleotide

<400> SEQUENCE: 19
tgtaccagca gctgaacgat                                                 20

<210> SEQ ID NO 20
<211> LENGTH: 20
<212> TYPE: DNA
<213> ORGANISM: Artificial
<220> FEATURE:
<223> OTHER INFORMATION: IFN-6 primer 2 oligonucleotide

<400> SEQUENCE: 20
cctcacagcc aggatgctat                                                 20

<210> SEQ ID NO 21
<211> LENGTH: 83
<212> TYPE: DNA
<213> ORGANISM: Artificial
<220> FEATURE:
<223> OTHER INFORMATION: IFN-F template oligonucleotide

<400> SEQUENCE: 21
ggctgtgagg aagtactttc agaggatcac cctgtacctg aaggagaaga agtacagccc    60
ttgcgcttgg gaagtcgtga ggg                                             83

<210> SEQ ID NO 22
<211> LENGTH: 20
```

```
<212> TYPE: DNA
<213> ORGANISM: Artificial
<220> FEATURE:
<223> OTHER INFORMATION: IFN-6b primer 1 oligonucleotide

<400> SEQUENCE: 22
atagcatcct ggctgtgagg                                                  20

<210> SEQ ID NO 23
<211> LENGTH: 20
<212> TYPE: DNA
<213> ORGANISM: Artificial
<220> FEATURE:
<223> OTHER INFORMATION: IFN-7 primer 1 oligonucleotide

<400> SEQUENCE: 23
atgatctcag ccctcacgac                                                  20

<210> SEQ ID NO 24
<211> LENGTH: 65
<212> TYPE: DNA
<213> ORGANISM: Artificial
<220> FEATURE:
<223> OTHER INFORMATION: IFN-G template oligonucleotide

<400> SEQUENCE: 24
ctgagatcat gaggagcttt agcctgagca ccaacctgca agagagcttg aggtctaagg      60
agtaa                                                                  65

<210> SEQ ID NO 25
<211> LENGTH: 20
<212> TYPE: DNA
<213> ORGANISM: Artificial
<220> FEATURE:
<223> OTHER INFORMATION: IFN-7b primer 1 oligonucleotide

<400> SEQUENCE: 25
gtcgtgaggg ctgagatcat                                                  20

<210> SEQ ID NO 26
<211> LENGTH: 36
<212> TYPE: DNA
<213> ORGANISM: Artificial
<220> FEATURE:
<223> OTHER INFORMATION: IFN-8 primer 2 oligonucleotide

<400> SEQUENCE: 26
tgctctagac ttttactcc ttagacctca agctct                                 36

<210> SEQ ID NO 27
<211> LENGTH: 69
<212> TYPE: DNA
<213> ORGANISM: Artificial
<220> FEATURE:
<223> OTHER INFORMATION: lysozyme signal peptide vector insert

<400> SEQUENCE: 27
ccaccatggg gtctttgcta atcttggtgc tttgcttcct gccgctagct gccttagggc      60
cctctagag                                                              69

<210> SEQ ID NO 28
<211> LENGTH: 671
<212> TYPE: DNA
<213> ORGANISM: Artificial
<220> FEATURE:
```

<223> OTHER INFORMATION: synthetic ovomucoid (MD) and ovotransferrin
       (OT) MDOT promoter linked to IFN-MM CDS, MDOT-IFN-MM sequence fragment

<400> SEQUENCE: 28

```
atcgataggt accgggcccc ccctcgaggt gaatatccaa gaatgcagaa ctgcatggaa     60
agcagagctg caggcacgat ggtgctgagc cttagctgct tcctgctggg agatgtggat    120
gcagagacga atgaaggacc tgtcccttac tcccctcagc attctgtgct atttagggtt    180
ctaccagagt ccttaagagg tttttttttt ttttggtcca aaagtctgtt tgtttggttt    240
tgaccactga gagcatgtga cacttgtctc aagctattaa ccaagtgtcc agccaaaatc    300
gatgtcacaa cttgggaatt ttccatttga agccccttgc aaaaacaaag agcaccttgc    360
ctgctccagc tcctggctgt gaagggtttt ggtgccaaag agtgaaaggc ttcctaaaaa    420
tgggctgagc cggggaaggg gggcaacttg gggctattg agaaacaagg aaggacaaac    480
agcgttaggt cattgcttct gcaaacacag ccagggctgc tcctctataa aaggggaaga    540
aagaggctcc gcagccatca cagacccaga ggggacggtc tgtgaatcaa gctttcacca    600
tggctttgac ctttgcctta ctggtggctc tcctggtgct gagctgcaag agcagctgct    660
cgtgggttgc g                                                         671
```

<210> SEQ ID NO 29
<211> LENGTH: 24
<212> TYPE: PRT
<213> ORGANISM: Artificial
<220> FEATURE:
<223> OTHER INFORMATION: MDOT-IFN-MM sequence fragment

<400> SEQUENCE: 29

```
Met Ala Leu Thr Phe Ala Leu Leu Val Ala Leu Leu Val Leu Ser Cys
1               5                   10                  15

Lys Ser Ser Cys Ser Trp Val Ala
            20
```

<210> SEQ ID NO 30
<211> LENGTH: 165
<212> TYPE: PRT
<213> ORGANISM: Artificial
<220> FEATURE:
<223> OTHER INFORMATION: synthetic transgenic poultry derived interferon-alpha 2b (TPD INF-alpha 2b)

<400> SEQUENCE: 30

```
Cys Asp Leu Pro Gln Thr His Ser Leu Gly Ser Arg Arg Thr Leu Met
  1               5                  10                  15

Leu Leu Ala Gln Met Arg Arg Ile Ser Leu Phe Ser Cys Leu Lys Asp
             20                  25                  30

Arg His Asp Phe Gly Phe Pro Gln Glu Glu Phe Gly Asn Gln Phe Gln
         35                  40                  45

Lys Ala Glu Thr Ile Pro Val Leu His Glu Met Ile Gln Gln Ile Phe
     50                  55                  60

Asn Leu Phe Ser Thr Lys Asp Ser Ser Ala Ala Trp Asp Glu Thr Leu
 65                  70                  75                  80

Leu Asp Lys Phe Tyr Thr Glu Leu Tyr Gln Gln Leu Asn Asp Leu Glu
                 85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
```

-continued

```
                115                 120                 125
Tyr Leu Lys Glu Lys Lys Tyr Ser Pro Cys Ala Trp Glu Val Val Arg
            130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 31
<211> LENGTH: 18
<212> TYPE: PRT
<213> ORGANISM: Artificial
<220> FEATURE:
<223> OTHER INFORMATION: lysozyme signal peptide

<400> SEQUENCE: 31

Met Gly Ser Leu Leu Ile Leu Val Leu Cys Phe Leu Pro Leu Ala Ala
  1               5                  10                  15

Leu Gly
```